(12) United States Patent
Phiasivongsa et al.

(10) Patent No.: US 11,667,641 B2
(45) Date of Patent: Jun. 6, 2023

(54) CRYSTALLINE FORMS OF 2-[3-[4-AMINO-3-(2-FLUORO-4-PHENOXYPHENYL)-1H-PYRAZOLO[3,4-D]PYRIMIDIN-1-YL]PIPERIDINE-1-CARBONYL]-4,4-DIMETHYLPENT-2-ENENITRILE

(71) Applicant: Principia Biopharma Inc., South San Francisco, CA (US)

(72) Inventors: Pasit Phiasivongsa, Hillsborough, CA (US); Jiang Zhu, San Ramon, CA (US); Kolbot By, San Ramon, CA (US); Mohammad Reza Masjedizadeh, San Jose, CA (US)

(73) Assignee: Principia Biopharma Inc., Bridgewater, NJ (US)

( * ) Notice: Subject to any disclaimer, the term of this patent is extended or adjusted under 35 U.S.C. 154(b) by 101 days.

(21) Appl. No.: 17/143,355

(22) Filed: Jan. 7, 2021

(65) Prior Publication Data
US 2021/0206772 A1    Jul. 8, 2021

Related U.S. Application Data

(60) Provisional application No. 62/958,389, filed on Jan. 8, 2020.

(51) Int. Cl.
*A61K 31/519* (2006.01)
*C07D 487/04* (2006.01)

(52) U.S. Cl.
CPC ........ *C07D 487/04* (2013.01); *C07B 2200/13* (2013.01)

(58) Field of Classification Search
CPC ............................ A61K 31/519; C07D 487/04
USPC ......................................... 514/262.1; 544/262
See application file for complete search history.

(56) References Cited

U.S. PATENT DOCUMENTS 8,946,241 B2 *    2/2015   Goldstein ............ A61K 9/2018
                                                          514/262.1

FOREIGN PATENT DOCUMENTS

WO      2012158764 A1    11/2012
WO      2022081512 A1     4/2022

OTHER PUBLICATIONS

International Search Report and Written Opinion for PCT/US2021/012515 dated Mar. 12, 2021 (14 pages).
Caira, Mino R., "Crystalline Polymorphism of Organic Compounds", Topics in Current Chemistry, Springer, Berlin, DE, vol. 198, pp. 163-208, Jan. 1, 1998.
Ahmed, A., et al., "Magnitude of benefit for topical crisaborole in the treatment of atopic dermatitis in children and adults does not look promising: a critical appraisal," British Journal of Dermatology, vol. 178, pp. 659-662 (2018).
Bennett, J.M., et al., "Inflammation—Nature's Way to Efficiently Respond to All Types of Challenges: Implications for Understanding and Managing "the Epidemic" of Chronic Diseases," Frontiers in Medicine (Lausanne), vol. 5, p. 316 (2018).
Bieber, T., "Atopic dermatitis," Annals of Dermatology, vol. 22, No. 2, pp. 125-137 (2010).
Bieber, T., et al., "Clinical phenotypes and endophenotypes of atopic dermatitis: Where are we, and where should we go?," Journal of Allergy Clinical Immunology, vol. 139, No. 4S, pp. S58-S64 (2017).
Bissonnette, R., et al., "Crisaborole and atopic dermatitis skin biomarkers: An intrapatient randomized trial," Journal of Allergy and Clinical Immunology, vol. 144, No. 5, pp. 1274-1289 (2019).
Bizikova, P., et al., "Cloning and establishment of canine desmocollin-1 as a major autoantigen in canine pemphigus foliaceus," Veterinary Immunology and Immunopathology, vol. 149, pp. 197-207 (2012).
Bizikova, P., et al., "Serum autoantibody profiles of IgA, IgE, and IgM in canine pemphigus foliaceus," Veterinary Dermatology, vol. 25, No. 5, p. 471 (2014).
Boguniewicz, M., et al., "Atopic dermatitis: a disease of altered skin barrier and immune dysregulation," Immunology Review, vol. 242, No. 1, pp. 233-246 (2011).

(Continued)

*Primary Examiner* — Douglas M Willis
(74) *Attorney, Agent, or Firm* — McNeill Baur PLLC

(57) ABSTRACT

Crystalline forms of Compound (I):

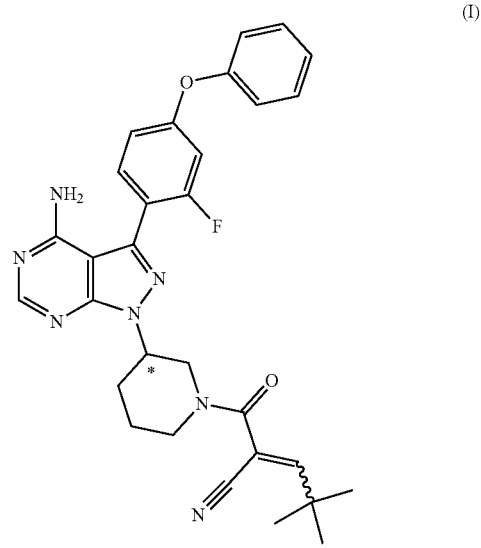

are disclosed. Pharmaceutical compositions comprising the same, methods of inhibiting BTK using the same, and methods for making crystalline forms of Compound (I) are also disclosed.

6 Claims, 10 Drawing Sheets

(56) References Cited

OTHER PUBLICATIONS

Boguniewicz, M., et al., "Expert Perspectives on Management of Moderate-to-Severe Atopic Dermatitis: A Multidisciplinary Consensus Addressing Current and Emerging Therapies," Journal of Allergy Clinical Immunology Practice, vol. 5, No. 6, pp. 1519-1531 (2017).

Byrd, J.C., et al., "Targeting BTK with Ibrutinib in Relapsed Chronic Lymphocytic Leukemia," New England Journal of Medicine, vol. 369, pp. 32-42 (2013).

Capen, C.C., "Mechanisms of chemical injury of the thyroid gland," Progress in Clinical and Biological Research, vol. 387, pp. 173-191 (1994).

Chang, B.Y., et al., "The Bruton tyrosine kinase inhibitor PCI-32765 ameliorates autoimmune arthritis by inhibition of multiple effector cells," Arthritis Research & Therapy, vol. 13, p. R115 (2011).

Crofford, L.J., et al.,"The role of Bruton's tyrosine kinase in autoimmunity and implications for therapy," Expert Review of Clinical Immunology, vol. 12, No. 7, pp. 763-113 (2016).

Curran, P.G., et al., "The effect of hepatic enzyme-inducing drugs on thyroid hormones and the thyroid gland," Endocrinology, vol. 12, No. 2, pp. 135-150 (1991).

Di Paolo, J.A., et al., "Specific Btk inhibition suppresses B cell- and myeloid cell-mediated arthritis," Nature Chemical Biology, vol. 7, pp. 41-50 (2011).

Eichenfield, L.F., et al., "Guidelines of care for the management of atopic dermatitis: section 2. Management and treatment of atopic dermatitis with topical therapies," Journal of the American Academy of Dermatology, vol. 71, No. 1, pp. 116-132 (2014).

Futatani, T., et al., "Brutons tyrosine kinase is present in normal platelets and its absence identifies patients with X-linked agammaglobulinaemia and carrier females," British Journal of Hematology, vol. 114, No. 1, pp. 141-149 (2001).

Goodale, E.C., et al., "Efficacy of a Bruton's Tyrosine Kinase Inhibitor (PRN-473) in the treatment of canine pemphigus foliaceus," Veterinary Dermatology, vol. 31, No. 4, p. 291 (2020).

Hanifin, J.M., et al., "Diagnostic features of atopic dermatitis," Acta Dermato-Venereologica Supplement (Stockholm), vol. 92, pp. 44-47 (1980).

Herter, J.M., et al., "PRN473, an inhibitor of Bruton's tyrosine kinase, inhibits neutrophil recruitment via inhibition of macrophage antigen-1 signalling," British Journal of Pharmacology, vol. 175, No. 3, pp. 429-439 (2018).

Honigberg, L.A., et al., "The Bruton tyrosine kinase inhibitor PCI-32765 blocks B cell activation and is efficacious in models of autoimmune disease and B cell malignancy," PNAS, vol. 107, pp. 13075-13080 (2010).

Hutcheson, J., et al., "Modulating proximal cell signaling by targeting Btk ameliorates humoral autoimmunity and endorgan disease in murine lupus," Arthritis Research & Therapy, vol. 14, p. R243 (2012).

Ihrke, P.J., et al., "Pemphigus foliaceus in dogs: a review of 37 cases," Journal of the American Veterinary Medical Association, vol. 186, No. 1, pp. 59-66 (1985).

International Preliminary Report on Patentability issued for PCT/US2021/012515 dated Jul. 21, 2022 (8 pages).

Irwin, S., "Comprehensive observational assessment: la. A systematic, quantitative procedure for assessing the behavioral and physiologic state of the mouse," Psychopharmacologia, vol. 13, No. 3, pp. 222-257 (1968).

Kim, K.H., et al., "lmidazo[1,5-a]quinoxalines as irreversible BTK inhibitors for the treatment of rheumatoid arthritis," Bioorganic & Medicinal Chemistry Letters, vol. 21, No. 21, pp. 6258-6263 (2011).

Lebakken, C.S., et al., "Development and application of a broad-coverage, TR-FRET-based kinase binding assay platform," Journal of Biomolecular Screening, vol. 14, pp. 924-935 (2009).

Maronpot, R.R., et al., "Hepatic Enzyme Induction: Histopathology," Toxicologic Pathology, vol. 38, No. 5, pp. 776-795 (2010).

Mohamed, A.J., et al., "Bruton's tyrosine kinase (Btk): function, regulation, and transformation with special emphasis on the PH domain," Immunology Review, vol. 228, pp. 58-73 (2009).

Oliveira, S., et al., "Neutrophil migration in infection and wound repair: going forward in reverse," Nature Reviews Immunology, vol. 16, No. 6, pp. 378-391 (2016).

Outerbridge, C., et al., A New Treatment for Autoimmune Blistering Diseases: Efficacy of the Bruton's Tyrosine Kinase (BTK) Inhibitor PRN473 in Canine Pemphigus Foliaceus, Poster #3530, 74th Annual Meeting, American Academy of Dermatology (AAD), Washington, D.C, Mar. 2016.

Patel, K.R., et al., "Association between atopic dermatitis, depression, and suicidal ideation: A systematic review and meta-analysis," Journal of the American Academy of Dermatology, vol. 80, No. 2, pp. 402-410 (2019).

Petersen, L.J., et al., "Histamine is released in the wheal but not the flare following challenge of human skin in vivo: a microdialysis study," Clinical & Experimental Allergy, vol. 27, No. 3, pp. 284-329 (1997).

Press Release, "Sanofi to acquire Principia Biopharma," Aug. 17, 2020.

Rip, J., et al., "The role of Bruton's Tyrosine Kinase in immune cell signaling and systemic autoimmunity," Critical Reviews in Immunology, vol. 38, No. 1, pp. 17-62 (2018).

Sideras, P., et al., "Molecular and cellular aspects of X-linked agammaglobulinemia," Advanced Immunology, vol. 59, pp. 135-223 (1995).

Silverberg, J.I., "Public Health Burden and Epidemiology of Atopic Dermatitis," Dermatologic Clinics, vol. 35, No. 3, pp. 283-289 (2017).

Silverberg, J.I., "Selected comorbidities of atopic dermatitis: Atopy, neuropsychiatric, and musculoskeletal disorders," Clinical Dermatology, vol. 35, No. 4, pp. 360-366 (2017).

Silverberg, J.I., et al., "Patient burden and quality of life in atopic dermatitis in US adults: A population-based cross-sectional study," Annals of Allergy, Asthma & Immunology, vol. 121, No. 3, pp. 340-347 (2018).

Spiewak, R., "Inter- and intra-individual variability of skin reactivity to histamine at prick-testing," Dermatology Online Journal, vol. 1, No. 1 (1995).

Trial Registration No. ACTRN12613000951752, "A Phase I, Randomised, Double-Blind, Placebo-Controlled, Ascending Single- and Repeat-Dose Study of the Safety, Tolerability and Pharmacokinetics of Orally Administered PRN473," Australian New Zealand Clinical Trials Registry, Aug. 27, 2013.

Trial Registration No. ACTRN12620000264298, "A Healthy Volunteer Study Evaluating the Tolerability and Pharmacokinetics of PRN473 Topical," Australian New Zealand Clinical Trials Registry, Feb. 28, 2020.

Trial Registration No. ACTRN12620000693921, "An interventional study to evaluate the effect and safety of PRN473 topical on skin reactions of otherwise healthy participants with allergies to common allergens," Australian New Zealand Clinical Trials Registry, Jun. 22, 2020.

Volmering, S., et al., "The Neutrophil Btk Signalosome Regulates Integrin Activation during Sterile Inflammation," Immunity, vol. 44, No. 1, pp. 73-87 (2016).

Weidinger, S., et al., "Atopic dermatitis," Nature Reviews Disease Primers, vol. 4, No. 1, p. 1 (2018).

Werfel, T., et al., "Cellular and molecular immunologic mechanisms in patients with atopic dermatitis," Journal of Allergy and Clinical Immunology, vol. 138, No. 2, pp. 336-349 (2016).

Xu, D., et al. "RN486, a selective Bruton's tyrosine kinase inhibitor, abrogates immune hypersensitivity responses and arthritis in rodents,"Journal of Pharmacology and Experimental Therapeutics, vol. 341, pp. 90-103 (2012).

Zane, L.T., et al., "Tolerability of crisaborole ointment for application on sensitive skin areas: A randomized, double-blind, vehicle-controlled study in healthy volunteers," American Journal of Clinical Dermatology, vol. 17, pp. 519-526 (2016).

\* cited by examiner

CRYSTALLINE FORMS OF 2-[3-[4-AMINO-3-(2-FLUORO-4-PHENOXYPHENYL)-1H-PYRAZOLO[3,4-D]PYRIMIDIN-1-YL]PIPERIDINE-1-CARBONYL]-4,4-DIMETHYLPENT-2-ENENITRILE

This application claims the benefit of priority to U.S. Provisional Application No. 62/958,389, filed Jan. 8, 2020, the contents of which are incorporated by reference herein in their entirety.

Disclosed herein are crystalline forms of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (Compound (I)), methods of using the same, and processes for making Compound (I), including its various crystalline forms. The crystalline forms of Compound (I) are inhibitors of Bruton's tyrosine kinase (BTK). The enzyme BTK is a member of the Tec family non-receptor tyrosine kinases.

BTK is expressed in most hematopoietic cells, including B cells, mast cells, and macrophages. BTK plays a role in the development and activation of B cells and has been implicated in multiple signaling pathways across a wide range of immune-mediated diseases. BTK activity has been implicated in the pathogenesis of several disorders and conditions, such as B cell-related hematological cancers (e.g., non-Hodgkin lymphoma and B cell chronic lymphocytic leukemia) and autoimmune diseases (e.g., rheumatoid arthritis, Sjogren's syndrome, pemphigus, IBD, lupus, and asthma).

Compound (I) and various solid forms thereof may inhibit BTK and be useful in the treatment of disorders and conditions mediated by BTK activity. Compound (I) is disclosed as, e.g., Compound 125A in Table 1 of WO 2012/158764 and has the following structure:

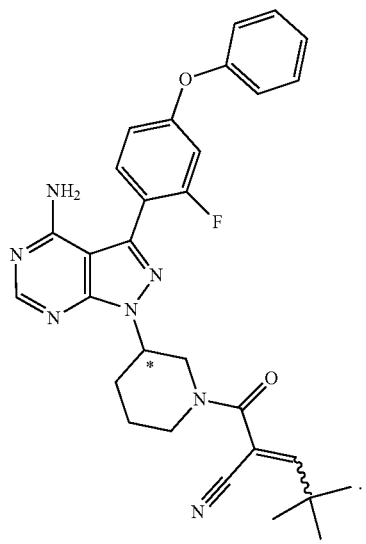

Solid forms (e.g., crystalline forms) of bioactive compounds, such as Compound (I), are of interest in the pharmaceutical industry, where solid forms with specific physical, chemical, or pharmaceutical properties, such as solubility, dissociation, true density, dissolution, melting point, morphology, compaction behavior, particle size, flow properties, or solid state stability, may be desirable or even required for pharmaceutical development. Crystalline forms occur where the same composition of matter crystallizes in different lattice arrangements, resulting in different thermodynamic properties and stabilities specific to each crystalline form. Each unique crystal form is known as a "polymorph."

While polymorphs of a given substance have the same chemical composition, they may differ from each other with respect to at least one physical, chemical, and/or pharmaceutical property, such as solubility, dissociation, true density, dissolution, melting point, crystal habit or morphology, compaction behavior, particle size, flow properties, and/or solid state stability. The solid-state form of a bioactive compound often determines its ease of preparation, ease of isolation, hygroscopicity, stability, solubility, storage stability, ease of formulation, rate of dissolution in gastrointestinal fluids, and in vivo bioavailability.

It is not yet possible to predict the possible solid forms (e.g., crystalline forms) of a compound, whether any such forms will be suitable for commercial use in a pharmaceutical composition, or which form or forms will display desirable properties. Because different solid forms (e.g., crystalline forms) may possess different properties, reproducible processes for producing a substantially pure solid form are also desirable for bioactive compounds intended for use as pharmaceuticals.

Accordingly, there is a need for novel solid forms, including novel crystalline forms, which are useful for treating disorders and conditions mediated by BTK activity, e.g., Compound (I), and reproducible, scalable methods of making the same.

Disclosed herein are novel crystalline forms of Compound (I), compositions comprising the same, and methods of using and making the same. In some embodiments, the novel crystalline forms disclosed herein have properties that are useful for large-scale manufacturing, pharmaceutical formulation, and/or storage. In some embodiments, the novel crystalline forms disclosed herein consist of one crystalline form. In some embodiments, the crystalline forms are substantially pure.

Some embodiments of the disclosure relate to a pharmaceutical composition comprising: a pharmaceutically acceptable excipient; and at least one crystalline form which is chosen from crystalline forms of Compound (I). In some embodiments, the at least one crystalline form is crystalline Form (I) of Compound (I). In some embodiments, the at least one crystalline form is crystalline Form (II) of Compound (I). In some embodiments, the at least one crystalline form is crystalline Form (III) of Compound (I). In some embodiments, the at least one crystalline form is crystalline Form (IV) of Compound (I). In some embodiments, the at least one crystalline form is crystalline Form (V) of Compound (I).

Some embodiments of the disclosure relate to methods of inhibiting BTK in a mammal in need of BTK inhibition by administering a therapeutically effective amount of at least one crystalline form chosen from crystalline forms of Compound (I). In some embodiments, the at least one crystalline form is crystalline Form (I) of Compound (I). In some embodiments, the at least one crystalline form is crystalline Form (II) of Compound (I). In some embodiments, the at least one crystalline form is crystalline Form (III) of Compound (I). In some embodiments, the at least one crystalline form is crystalline Form (IV) of Compound (I). In some embodiments, the at least one crystalline form is crystalline Form (V) of Compound (I).

In some embodiments, the mammal in need of BTK inhibition is suffering from a disease mediated by BTK. In some embodiments, the disease mediated by BTK is chosen from pemphigus vulgaris, pemphigus foliaceus, immune thrombocytopenia, cutaneous lupus, cutaneous lupus erythematosus, dermatitis, alopecia areata, vitiligo, pyoderma gangrenosum, membrane pemphigoid, epidermolysis bullosa acquisita, Steven Johnson Syndrome, TEN Toxic epidermal necrolysis, drug eruptions, folliculitis decalvans, pseudofolliculitis barbae, leucoclastic vasculitis, hidradenitis supprativa, palmar platar pustulosis, Lichenoid dermatitis, acne, mycosis fungoides, sweet syndrome, inflammatory bowel disease, arthritis, lupus, lupus nephritis, rheumatoid arthritis, psoriatic arthritis, juvenile arthritis, Sjogren's syndrome, multiple sclerosis, ankylosing spondylitisis, scleroderma, Wegener's granulomatosis, psoriasis, asthma, colitis, conjunctivitis, dermatitis, uveitis, eczema, diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, non-Hodgkin lymphoma, intravascular large B cell lymphoma, primary effusion lymphoma, burkitt lymphoma/leukemia, and lymphomatoid granulomatosis.

In some embodiments, the disease mediated by BTK is chosen from pemphigus vulgaris. In some embodiments, the disease mediated by BTK is chosen from pemphigus *foliaceus*.

In some embodiments, the mammal in need of BTK inhibition is a human. In some embodiments, the mammal in need of BTK inhibition is a canine.

Also disclosed herein are methods of preparing at least one crystalline form chosen from crystalline forms of Compound (I). Some embodiments of the disclosure are directed to said methods, wherein the at least one crystalline form is crystalline Form (I) of Compound (I). Some embodiments of the disclosure are directed to said methods, wherein the at least one crystalline form is crystalline Form (II) of Compound (I). Some embodiments of the disclosure are directed to said methods, wherein the at least one crystalline form is crystalline Form (III) of Compound (I). Some embodiments of the disclosure are directed to said methods, wherein the at least one crystalline form is crystalline Form (IV) of Compound (I). Some embodiments of the disclosure are directed to said methods, wherein the at least one crystalline form is crystalline Form (V) of Compound (I).

In some embodiments, the methods comprise temperature-cycled ripening of a slurry comprising Compound (I). In some embodiments, the slurry comprising Compound (I) is temperature cycled between 5° C. and 40° C. In some embodiments, the slurry comprising Compound (I) is temperature cycled for 36 hours. In some embodiments, the slurry comprising Compound (I) is temperature cycled for 36 hours between 5° C. and 40° C. In some embodiments, the slurry is equilibrated after temperature-cycled ripening. In some embodiments, the slurry is equilibrated at 25° C. In some embodiments, the slurry is equilibrated for eight hours. In some embodiments, the slurry further comprises at least one solvent chosen from 1-butanol, 1-methoxy-2-propanol, 1-propanol, 2-methoxyethanol, 2-methoxyethyl ether, 4-methyl-2-pentanone acetone, acetonitrile, butyl acetate, cyclohexane, cyclopentyl methyl ether, ethanol, ethyl acetate, heptane, isopropyl acetate, isopropyl ether, isopropyl ethyl ether, methanol, nitromethane, N,N-dimethylformamide, t-butyl methyl ether, trifluoroethanol, and water.

In some embodiments, the methods comprise rapidly cooling a clarified saturated solution comprising Compound (I). In some embodiments, the clarified saturated solution comprising Compound (I) was rapidly cooled from 25° C. to 4° C. In some embodiments, the clarified saturated solution comprising Compound (I) was held after rapidly cooling. In some embodiments, the clarified saturated solution comprising Compound (I) was held at 4° C. In some embodiments, the clarified saturated solution comprising Compound (I) was held for 48 hours. In some embodiments, the clarified saturated solution comprising Compound (I) was held at 4° C. for 48 hours. In some embodiments, the clarified saturated solution comprising Compound (I) further comprises 2-butanone.

In some embodiments, the methods comprise slowly evaporating a solution comprising Compound (I). In some embodiments, the solution comprising Compound (I) is slowly evaporated for up to ten days. In some embodiments, the solution comprising Compound (I) further comprises at least one solvent chosen from 1-butanol, 1-methoxy-2-propanol, 2-methyltetrahydrofuran, 1-propanol, 2-butanone, 2-methoxyethanol, acetone, acetonitrile, cyclopentyl methyl ether, ethanol, ethyl acetate, isopropyl acetate, isopropyl ether, methanol, nitromethane, toluene, and water.

EMBODIMENTS

Figure 1:
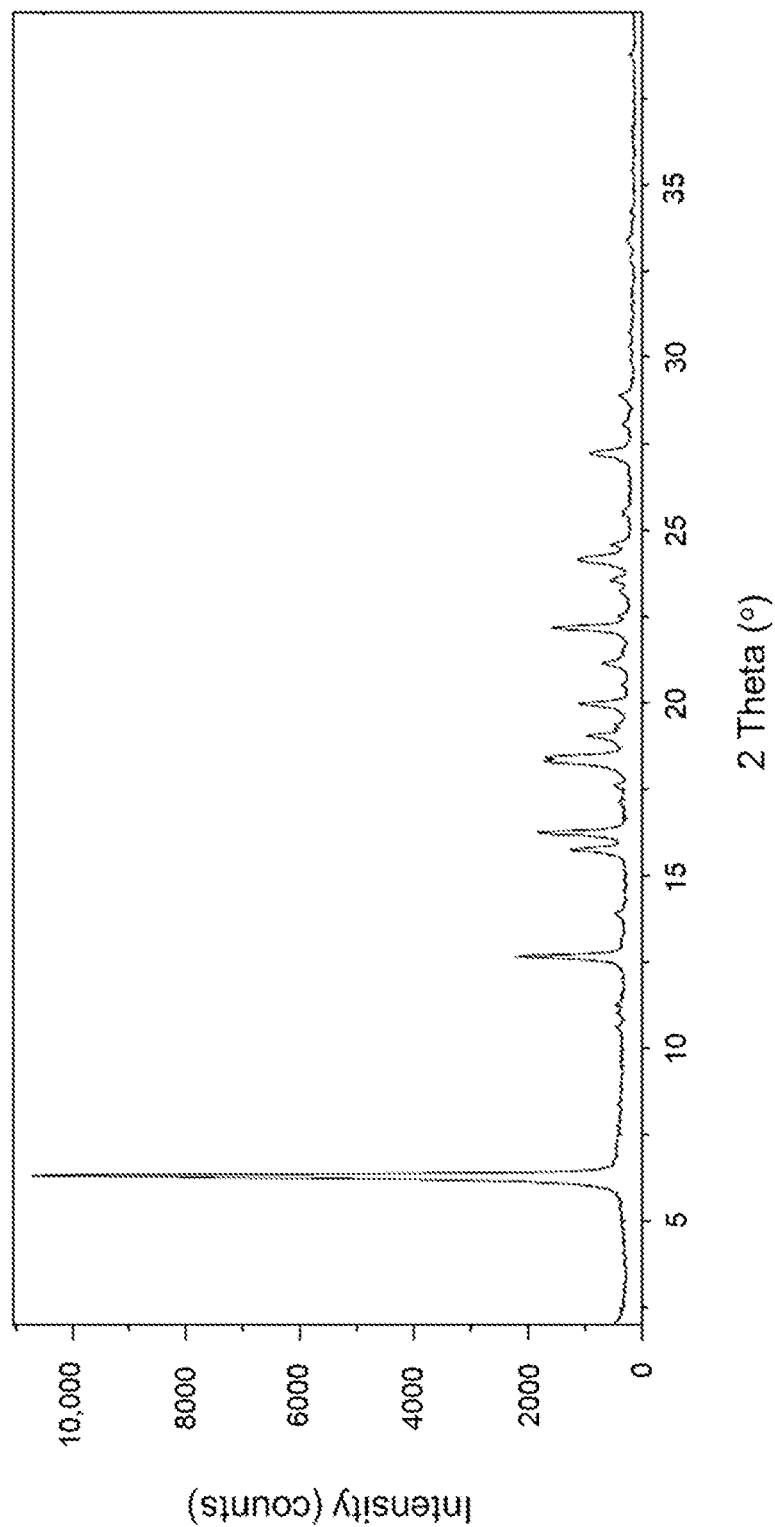
FIG. 1 shows an X-ray powder diffractogram for crystalline Form (I) of Compound (I), referred to as crystalline Form (I) herein, showing degrees 2θ (2-theta) on the X-axis and relative intensity on the Y-axis.

Non-limiting embodiments of this disclosure include:

1. Crystalline Form (I) of Compound (I):

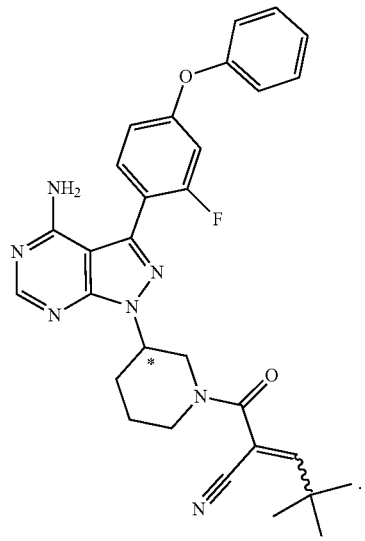 [SMILES: CC(C)(C)C=C(C#N)C(=O)N1CCCC(n2nc(-c3ccc(Oc4ccccc4)cc3F)c3c(N)ncnc32)C1]

(I)

2. Crystalline Form (I) according to Embodiment 1, characterized by an X-ray powder diffractogram having a signal at at least three two-theta values chosen from 6.3±0.2, 12.6±0.2, 16.2±0.2, 17.6±0.2, 18.2±0.2, 18.4±0.2, and 22.1±0.2.

3. Crystalline Form (I) according to Embodiment 1, characterized by an X-ray powder diffractogram substantially similar to that in FIG. 1.

4. Crystalline Form (I) according to any one of Embodiments 1 to 3, characterized by a DSC thermogram having a peak endotherm (melting temperature) at about 177° C. to about 178° C.

5. Crystalline Form (I) according to any one of Embodiments 1 to 4, characterized by a DSC thermogram showing onset of melting at about 174.8° C. to about 175.2° C.

6. Crystalline Form (I) according to any one of Embodiments 1 to 5, wherein at least 95% by weight of Compound (I) is the (E) isomer.

7. Crystalline Form (I) according to any one of Embodiments 1 to 6, wherein at least 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

8. Crystalline Form (I) of Compound (I) prepared by a process comprising:

adding methyl isobutyl ketone to amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile to form a solution;

agitating the solution to form a precipitate; and isolating crystalline Form (I) by filtration.

9. Crystalline Form (II) of Compound (I):

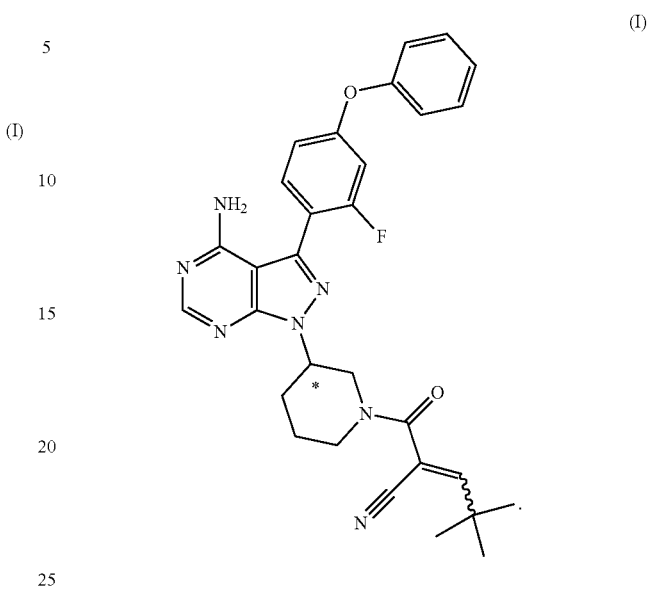

(I)

10. Crystalline Form (II) according to Embodiment 9, characterized by an X-ray powder diffractogram having a signal at at least three two-theta values chosen from 6.3±0.2, 15.2±0.2, 16.0±0.2, 16.6±0.2, 17.7±0.2, 20.0±0.2, 24.8±0.2, and 27.5±0.2.

11. Crystalline Form (II) according to Embodiment 9, characterized by an X-ray powder diffractogram substantially similar to that in FIG. 3.

12. Crystalline Form (II) according to any one of Embodiments 9 to 11, characterized by a DSC thermogram having a peak endotherm (melting temperature) at about 170.0° C. to about 170.2° C.

13. Crystalline Form (II) according to any one of Embodiments 9 to 12, characterized by a DSC thermogram showing an onset of melting at about 167.2° C. to about 167.6° C.

14. Crystalline Form (II) according to any one of Embodiments 9 to 13, characterized by a mass loss of less than 1.5 wt. % between 35° C. and 220° C. by thermogravimetric analysis.

15. Crystalline Form (II) according to any one of Embodiments 9 to 14, wherein at least 95% by weight of Compound (I) is the (E) isomer.

16. Crystalline Form (II) according to any one of Embodiments 9 to 15, wherein at least 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

17. Crystalline Form (II) of Compound (I) prepared by a process comprising:

dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether to form a solution;

stirring the solution to form a precipitate; and isolating crystalline Form (II) by filtration.

18. Crystalline Form (III) of Compound (I):

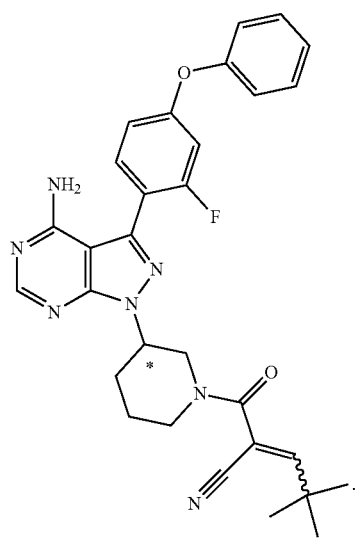

(I)

19. Crystalline Form (III) according to Embodiment 18, characterized by an X-ray powder diffractogram having a signal at at least three two-theta values chosen from 10.3±0.2, 15.1±0.2, 16.5±0.2, 17.6±0.2, 20.0±0.2, and 22.5±0.2.

20. Crystalline Form (III) according to Embodiment 18, characterized by an X-ray powder diffractogram substantially similar to that in FIG. 5.

21. Crystalline Form (III) according to any one of Embodiments 18 to 20, characterized by a DSC thermogram having a peak endotherm (melting temperature) at about 167.4° C. to about 167.8° C.

22. Crystalline Form (III) according to any one of Embodiments 18 to 21, characterized by a DSC thermogram showing an onset of melting at about 165.1° C. to about 165.5° C.

23. Crystalline Form (III) according to any one of Embodiments 18 to 22, wherein at least 95% by weight of Compound (I) is the (E) isomer.

24. Crystalline Form (III) according to any one of Embodiments 18 to 23, wherein at least 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

25. Crystalline Form (III) of Compound (I) prepared by a process comprising:

dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether; and isolating crystalline Form (III) by filtration.

26. Crystalline Form (IV) of Compound (I):

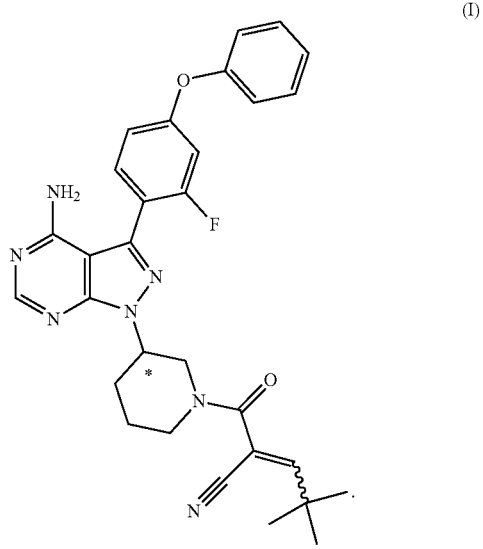 [SMILES: CC(C)(C)C=C(C#N)C(=O)N1CCCC(n2nc(-c3ccc(Oc4ccccc4)cc3F)c3c(N)ncnc32)C1]

(I)

27. Crystalline Form (IV) according to Embodiment 26, characterized by an X-ray powder diffractogram having a signal at at least three two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2.

28. Crystalline Form (IV) according to Embodiment 26, characterized by an X-ray powder diffractogram substantially similar to that in FIG. 7.

29. Crystalline Form (IV) according to any one of Embodiments 26 to 28, characterized by a mass loss of less than 14 wt. % between 70° C. and 180° C. by thermogravimetric analysis.

30. Crystalline Form (IV) according to any one of Embodiments 26 to 29, wherein at least 95% by weight of Compound (I) is the (E) isomer.

31. Crystalline Form (IV) according to any one of Embodiments 26 to 30, wherein at least 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

32. Crystalline Form (IV) of Compound (I) prepared by a process comprising:

dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in 2-methyl-1-propanol to form a solution;

filtering the solution; and isolating crystalline Form (IV) by evaporating the 2-methyl-1-propanol.

33. Crystalline Form (V) of Compound (I):

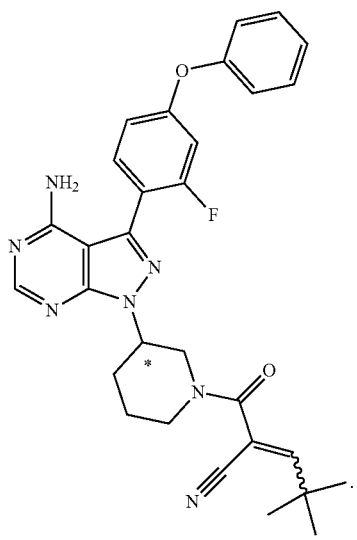

34. Crystalline Form (V) according to Embodiment 33, characterized by an X-ray powder diffractogram having a signal at at least three two-theta values chosen from 4.7±0.2, 6.5±0.2, 14.2±0.2, 16.2±0.2, 16.5±0.2, 19.8±0.2, and 20.7±0.2.

35. Crystalline Form (V) according to Embodiment 33, characterized by an X-ray powder diffractogram substantially similar to that in FIG. 9.

36. Crystalline Form (V) according to any one of Embodiments 33 to 35, characterized by a mass loss of less than 7 wt. % between 75° C. and 110° C. by thermogravimetric analysis.

37. Crystalline Form (V) according to any one of Embodiments 33 to 36, wherein at least 95% by weight of Compound (I) is the (E) isomer.

38. Crystalline Form (V) according to any one of Embodiments 33 to 37, wherein at least 95% by weight of Compound (I) is (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

39. Crystalline Form (V) of Compound (I) prepared by a process comprising:
    dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in toluene to form a solution;
    filtering the solution; and
    isolating crystalline Form (V) by evaporating the toluene.

40. A pharmaceutical composition comprising:
    at least one pharmaceutically acceptable excipient; and
    at least one crystalline form chosen from the crystalline forms of any one of Embodiments 1 to 39.

41. A method of inhibiting Bruton's tyrosine kinase (BTK) in a mammal in need of BTK inhibition comprising administering to the mammal a therapeutically effective amount of at least one crystalline form chosen from the crystalline forms of any one of Embodiments 1 to 39.

42. A method of treating a disease mediated by BTK in a mammal in need thereof comprising administering to the mammal a therapeutically effective amount of at least one crystalline form chosen from the crystalline forms of any one of Embodiments 1 to 39.

43. The method of Embodiment 42, wherein the disease is chosen from pemphigus vulgaris, pemphigus foliaceus, immune thrombocytopenia, cutaneous lupus, cutaneous lupus erythematosus, dermatitis, alopecia areata, vitiligo, pyoderma gangrenosum, membrane pemphigoid, epidermolysis bullosa acquisita, Steven Johnson Syndrome, TEN Toxic epidermal necrolysis, drug eruptions, folliculitis decalvans, pseudofolliculitis barbae, leucoclastic vasculitis, hidradenitis supprativa, palmar platar pustulosis, Lichenoid dermatitis, acne, mycosis fungoides, sweet syndrome, inflammatory bowel disease, arthritis, lupus, lupus nephritis, rheumatoid arthritis, psoriatic arthritis, juvenile arthritis, Sjogren's syndrome, multiple sclerosis, ankylosing spondylitisis, scleroderma, Wegener's granulomatosis, psoriasis, asthma, colitis, conjunctivitis, dermatitis, uveitis, eczema, diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, non-Hodgkin lymphoma, intravascular large B cell lymphoma, primary effusion lymphoma, burkitt lymphoma/leukemia, and lymphomatoid granulomatosis.

44. The method according to any one of Embodiments 41 to 43, wherein the mammal is a human.

45. A method for preparing crystalline Form (I) of Compound (I) comprising:
    adding methyl isobutyl ketone to amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile to form a solution;
    agitating the solution to form a precipitate; and
    isolating crystalline Form (I) by filtration.

46. A method for preparing crystalline Form (II) of Compound (I) comprising:
    dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether to form a solution;
    stirring the solution to form a precipitate; and
    isolating crystalline Form (II) by filtration.

47. A method for preparing crystalline Form (III) of Compound (I) comprising:
    dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether; and
    isolating crystalline Form (III) by filtration.

48. A method for preparing crystalline Form (IV) of Compound (I) comprising:
    dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in 2-methyl-1-propanol to form a solution;
    filtering the solution; and
    isolating crystalline Form (IV) by evaporating the 2-methyl-1-propanol.

49. A method for preparing crystalline Form (V) of Compound (I) comprising:

dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in toluene to form a solution;

filtering the solution; and isolating crystalline Form (V) by evaporating the toluene.

Definitions

As used herein, "a" or "an" entity refers to one or more of that entity, e.g., "a compound" refers to one or more compounds or at least one compound unless stated otherwise. As such, the terms "a" (or "an"), "one or more," and "at least one" are used interchangeably herein.

As used herein, the term "about" or "approximately" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%.

As used herein, "Compound (I)" refers to the (E) isomer, (Z) isomer, or a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, (S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, or a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, which has the following structure:

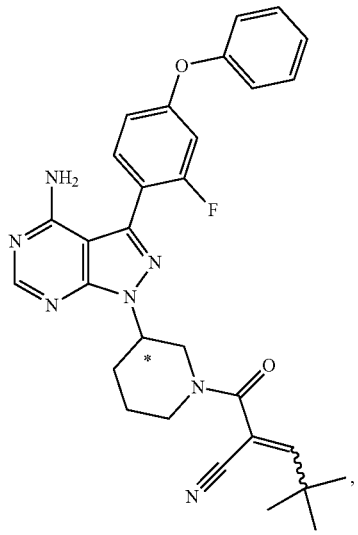

where *C is a stereochemical center.

When Compound (I) is denoted as (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, it may contain the corresponding (S) enantiomer as an impurity in less than 1% by weight. Accordingly, when the Compound (I) is denoted as a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, the amount of (R) or (S) enantiomer in the mixture is greater than 1% by weight. Similarly, when Compound (I) is denoted as the (E) isomer, it may contain the corresponding (Z) isomer as an impurity in less than 1% by weight. Accordingly, when the Compound (I) is denoted as a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile, the amount of (E) or (Z) isomer in the mixture is greater than 1% by weight.

In some embodiments, Compound (I) is a mixture of (R) and (S) enantiomers of 2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, Compound (I) is substantially (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least 75%, e.g., at least 80%, at least 85%, at least 90%, at least 95%, by weight (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least 95% by weight (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

Herein, Compound (I) may be referred to as a "drug," "active agent," "a therapeutically active agent," or a "API."

As used herein, "substantially pure" in connection with a geometric isomeric form refers to a compound, such as Compound (I), wherein more than 70% by weight of the compound is present as the given isomeric form. For example, the phrase "the crystalline Form (I) of Compound (I) is a substantially pure (E) isomer of Compound (I)" refers to the crystalline Form (I) of Compound (I) having at least 70% by weight of the crystalline Form (I) of Compound (I) being in the (E) isomeric form, and the phrase "the crystalline Form (I) of Compound (I) is a substantially pure (Z) isomer of Compound (I)" refers to the crystalline Form (I) of Compound (I) having at least 70% by weight of the crystalline Form (I) of Compound (I) being in the (Z) isomeric form. In some embodiments, at least 80% by weight of the crystalline form of Compound (I) is the (E) form or at least 80% by weight of the crystalline form of Compound (I) is the (Z) form. In some embodiments, at least 85% by weight of the crystalline form of Compound (I) is in the (E) form or at least 85% by weight of the crystalline form of Compound (I) is in the (Z) form. In some embodiments, at least 90% by weight of the crystalline form of Compound (I) is in the (E) form or at least 90% by weight of the crystalline form of Compound (I) is in the (Z) form. In some embodiments, at least 95% by weight of the crystalline form of Compound (I) is in the (E) form or at least 95% by weight of the crystalline form of Compound (I) is in the (Z) form. In some embodiments, at least 97% by weight of the crystalline form of Compound (I) is in the (E) form or at least 97% by weight of the crystalline form of Compound (I) is in the (Z) form. In some embodiments, at least 98% by weight of the crystalline form of Compound (I) is in the (E) form or at least 98% by weight of the crystalline form of Compound (I) is in the (Z) form. In some embodiments, at least 99% by weight of the crystalline form of Compound (I) is in the (E) form or at least 99% by weight of the crystalline form of Compound (I) is in the (Z) form. The relative amounts of (E) and (Z) isomers in a solid mixture can be determined according to standard methods and techniques known in the art.

In some embodiments, Compound (I) is a mixture of (E) and (Z) isomers of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

In some embodiments, Compound (I) is a substantially pure (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least 75%, e.g., at least 80%, at least 85%, at least 90%, at least 95%, by weight (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile. In some embodiments, Compound (I) is at least 95% by weight (E) isomer of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

As used herein, the terms "polymorph," "crystal form," "crystalline form," and "Form" interchangeably refer to a solid having a particular molecular packing arrangement in the crystal lattice. Crystalline forms can be identified and distinguished from each other by at least one characterization technique, including, e.g., X-ray powder diffraction (XRPD), single crystal X-ray diffraction, differential scanning calorimetry (DSC), dynamic vapor sorption (DVS), and/or thermogravimetric analysis (TGA). Accordingly, as used herein, the term "crystalline Form [X] of Compound (I)" refers to a unique crystalline form that can be identified and distinguished from other forms by at least one characterization technique, including, e.g., X-ray powder diffraction (XRPD), single crystal X-ray diffraction, differential scanning calorimetry (DSC), dynamic vapor sorption (DVS), and/or thermogravimetric analysis (TGA). In some embodiments, the novel crystalline forms of this disclosure are characterized by an X-ray powder diffractogram having at least one signal at least one specified two-theta value (°2θ).

As used herein, a "pharmaceutically acceptable excipient" refers to a carrier or an excipient that is useful in preparing a pharmaceutical composition. For example, a pharmaceutically acceptable excipient is generally safe and includes carriers and excipients that are generally considered acceptable for mammalian pharmaceutical use.

As used herein, "a therapeutically effective amount" of a compound disclosed herein refers to an amount of the compound that will elicit a biological or medical response in a subject. The therapeutically effective amount will depend on the purpose of the treatment and will be ascertainable by one of ordinary skill in the art (see, e.g., Lloyd (1999) The Art, Science and Technology of Pharmaceutical Compounding).

As used herein, the term "inhibit," "inhibition," or 'inhibiting" refers to the reduction or suppression of a given condition, symptom, or disorder, or disease, or a significant decrease in the baseline activity of a biological activity or process.

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art.

As used herein, a "mammal" refers to domesticated animals (e.g., dogs, cats, and horses) and humans. In some embodiments, the mammal is a human. In some embodiments, the mammal is a canine.

As used herein, the term "DSC" refers to the analytical method of differential scanning calorimetry.

As used herein, the term "TGA" refers to the analytical method of thermo gravimetric (also referred to as thermogravimetric) analysis.

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," and "XRPD pattern" refer to an experimentally obtained pattern plotting signal positions (on the abscissa) versus signal intensities (on the ordinate). For a crystalline material, an X-ray powder diffractogram may include at least one signal, each identified by its angular value as measured in degrees 2θ (°2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) chosen from . . . ."

A used herein, the term "X-ray powder diffractogram having a signal at . . . two-theta values" refers to an XRPD pattern that contains X-ray reflection positions as measured and observed in X-ray powder diffraction experiments (°2θ).

As used herein, the term "signal" refers to a point in the XRPD pattern where the intensity as measured in counts is at a local maximum. One of ordinary skill in the art would recognize that at least one signal in an XRPD pattern may overlap and may, for example, not be apparent to the naked eye. One of ordinary skill in the art would recognize that some art-recognized methods are capable of and suitable for determining whether a signal exists in a pattern, such as, e.g., Rietveld refinement.

As used herein, the terms "a signal at . . . degrees two-theta," "a signal at [a] two-theta value[ ] of . . . ," and "a signal at at least . . . two-theta value(s) chosen from . . . " refer to X-ray reflection positions as measured and observed in X-ray powder diffraction experiments (°2θ). In some embodiments, the repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta). It is well known to one of ordinary skill in the art that there can be variability in the measurements of X-ray powder diffraction signal values. As such, a person of ordinary skill in the art would appreciate that there may be variability of up to ±0.2 °2θ in signal value for the same signal in different samples. Additionally, it is well known to one of ordinary skill in the art that there can be variability in the measurements of relative signal intensities in X-ray powder diffraction experiments. Illustratively, non-limiting factors that can affect the relative signal intensities include sample thickness and preferred orientation (e.g., the crystalline particles are not distributed randomly).

As used herein, an X-ray powder diffractogram is "substantially similar to that in [a particular] FIG." when at least 90%, such as at least 95%, at least 98%, or at least 99%, of the signals in the two diffractograms are the same ±0.2 °2θ. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (°2θ) referred to herein) generally mean that value reported ±0.2 degrees 2θ of the reported value, an art-recognized variance discussed above.

As stated above, described herein are novel crystalline forms of Compound (I). These may be inhibitors of BTK. BTK inhibitors are useful in the treatment of diseases mediated by BTK, e.g., pemphigus vulgaris and pemphigus foliaceus.

Crystalline Form (I) of Compound (I)

In some embodiments, the present disclosure provides crystalline Form (I) of Compound (I):

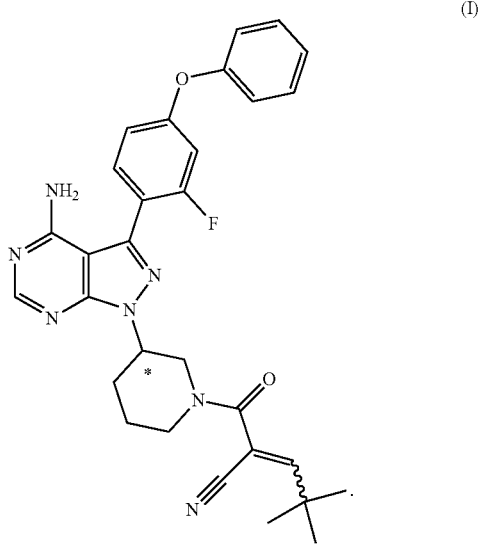 [SMILES: CC(C)(C)C=C(C#N)C(=O)N1CCCC(n2nc(-c3ccc(Oc4ccccc4)cc3F)c3c(N)ncnc32)C1]

(I)

FIG. 1 shows an X-ray powder diffractogram for crystalline Form (I) of Compound (I).

Figure 2:
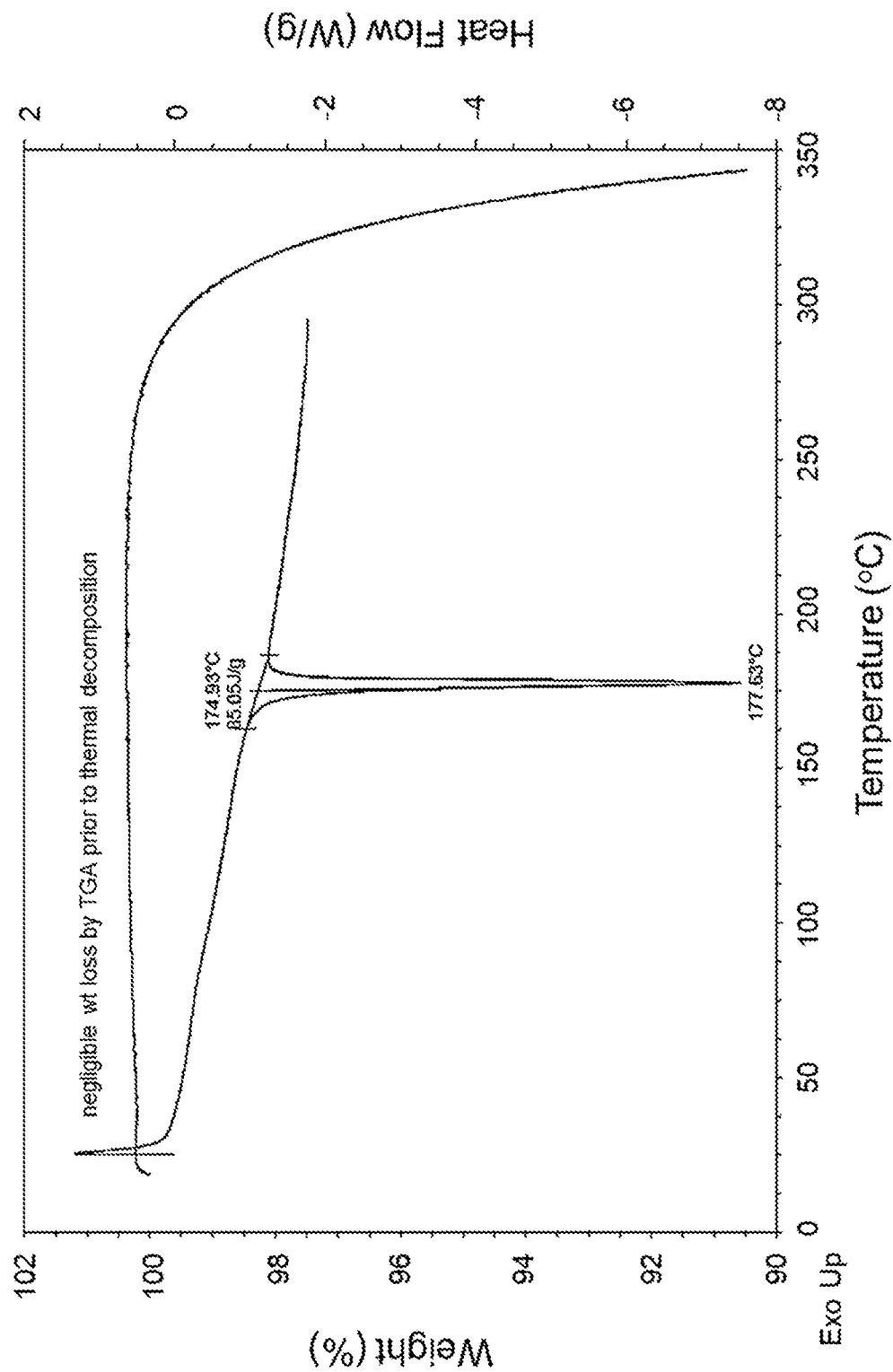
FIG. 2 shows a differential scanning calorimetry (DSC) thermogram and a thermogravimetric analysis (TGA) thermal curve for crystalline Form (I) of Compound (I).

FIG. 2 shows a DSC thermogram of crystalline Form (I) of Compound (I). In some embodiments, crystalline Form (I) of Compound (I) is characterized by a DSC thermogram having a peak endotherm (melting temperature) at about 177° C. to about 178° C. In some embodiments, crystalline Form (I) of Compound (I) is characterized by a DSC thermogram showing onset of melting/decomposition at about 174.8° C. to about 175.2° C. In some embodiments, crystalline Form (I) of Compound (I) is characterized by a DSC thermogram showing onset of melting at about 174.8° C. to about 175.2° C. In some embodiments, the associated enthalpy is about 85 J/g (ΔH=85 J/g).

In some embodiments, crystalline Form (I) of Compound (I) is characterized by a DSC thermogram substantially similar to that in FIG. 2.

FIG. 2 also shows a TGA thermal curve for crystalline Form (I) of Compound (I).

In some embodiments, crystalline Form (I) of Compound (I) is a white solid.

In some embodiments, crystalline Form (I) of Compound (I) is characterized by an X-ray powder diffractogram generated by an X-ray powder diffraction analysis with an incident beam of Cu Kα radiation with signals substantially similar to those recited in Table 1.

TABLE 1

| 2-theta (deg) |
| --- |
| 6.32 |
| 9.07 |
| 10.65 |
| 11.10 |
| 11.31 |
| 12.68 |
| 13.93 |
| 15.78 |
| 16.28 |
| 17.19 |
| 17.65 |
| 18.43 |
| 19.04 |
| 19.38 |
| 19.99 |
| 20.58 |
| 21.17 |
| 21.55 |
| 22.19 |
| 22.56 |
| 23.25 |
| 23.59 |
| 24.16 |
| 24.61 |
| 25.47 |
| 27.20 |
| 28.13 |
| 28.87 |
| 29.94 |
| 31.47 |
| 32.86 |
| 33.82 |
| 35.52 |
| 36.32 |

In some embodiments, crystalline Form (I) of Compound (I) is characterized by an X-ray powder diffractogram having a signal at 6.3±0.2 degrees two-theta. In some embodiments, crystalline Form (I) of Compound (I) is characterized by an X-ray powder diffractogram having a signal at 12.6±0.2 degrees two-theta. In some embodiments, crystalline Form (I) of Compound (I) is characterized by an X-ray powder diffractogram having a signal at 16.2±0.2 degrees two-theta. In some embodiments, crystalline Form (I) of Compound (I) is characterized by an X-ray powder diffractogram having a signal at 17.6±0.2 degrees two-theta. In some embodiments, crystalline Form (I) of Compound (I) is characterized by an X-ray powder diffractogram having a signal at 18.2±0.2 degrees two-theta. In some embodiments, crystalline Form (I) of Compound (I) is characterized by an X-ray powder diffractogram having a signal at 18.4±0.2 degrees two-theta. In some embodiments, crystalline Form (I) of Compound (I) is characterized by an X-ray powder diffractogram having a signal at 22.1±0.2 degrees two-theta.

In some embodiments, crystalline Form (I) of Compound (I) is characterized by an X-ray powder diffractogram having a signal at two-theta values of 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least six two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least five two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least four two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least three two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least two two-theta values chosen from 6.3±0.2, 12.6±0.2, 16.2±0.2, 17.6±0.2, 18.2±0.2, 18.4±0.2, and 22.1±0.2. In some embodiments, crystalline Form (I) of Compound (I) is characterized by an X-ray powder diffractogram having a signal at at least one two-theta value chosen from 6.3±0.2, 12.6±0.2, 16.2±0.2, 17.6±0.2, 18.2±0.2, 18.4±0.2, and 22.1±0.2.

In some embodiments, crystalline Form (I) of Compound (I) is characterized by an X-ray powder diffractogram substantially similar to that in FIG. 1.

In some embodiments, the present disclosure provides a process for preparing crystalline Form (I) of Compound (I). In some embodiments, the present disclosure provides crystalline Form (I) of Compound (I) prepared by a process comprising: adding methyl isobutyl ketone to amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile to form a solution. In some embodiments, the process further comprises agitating the solution to form a precipitate. In some embodiments, the process further comprises isolating crystalline Form (I) by filtration.

Crystalline Form (II) of Compound (I)

In some embodiments, the present disclosure provides crystalline Form (II) of Compound (I):

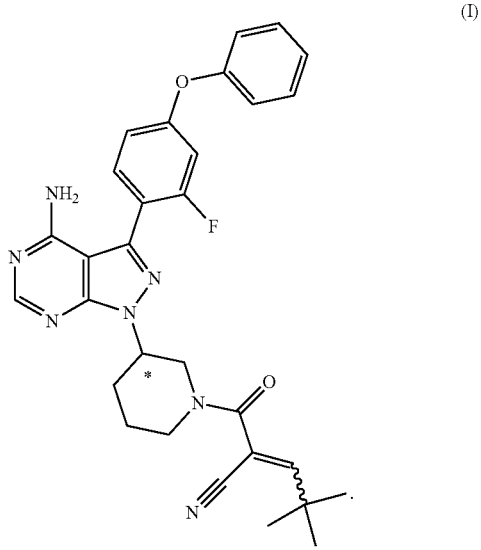 [SMILES: CC(C)(C)C=C(C#N)C(=O)N1CCCC(n2nc(-c3ccc(Oc4ccccc4)cc3F)c3c(N)ncnc32)C1]

(I)

Figure 3:
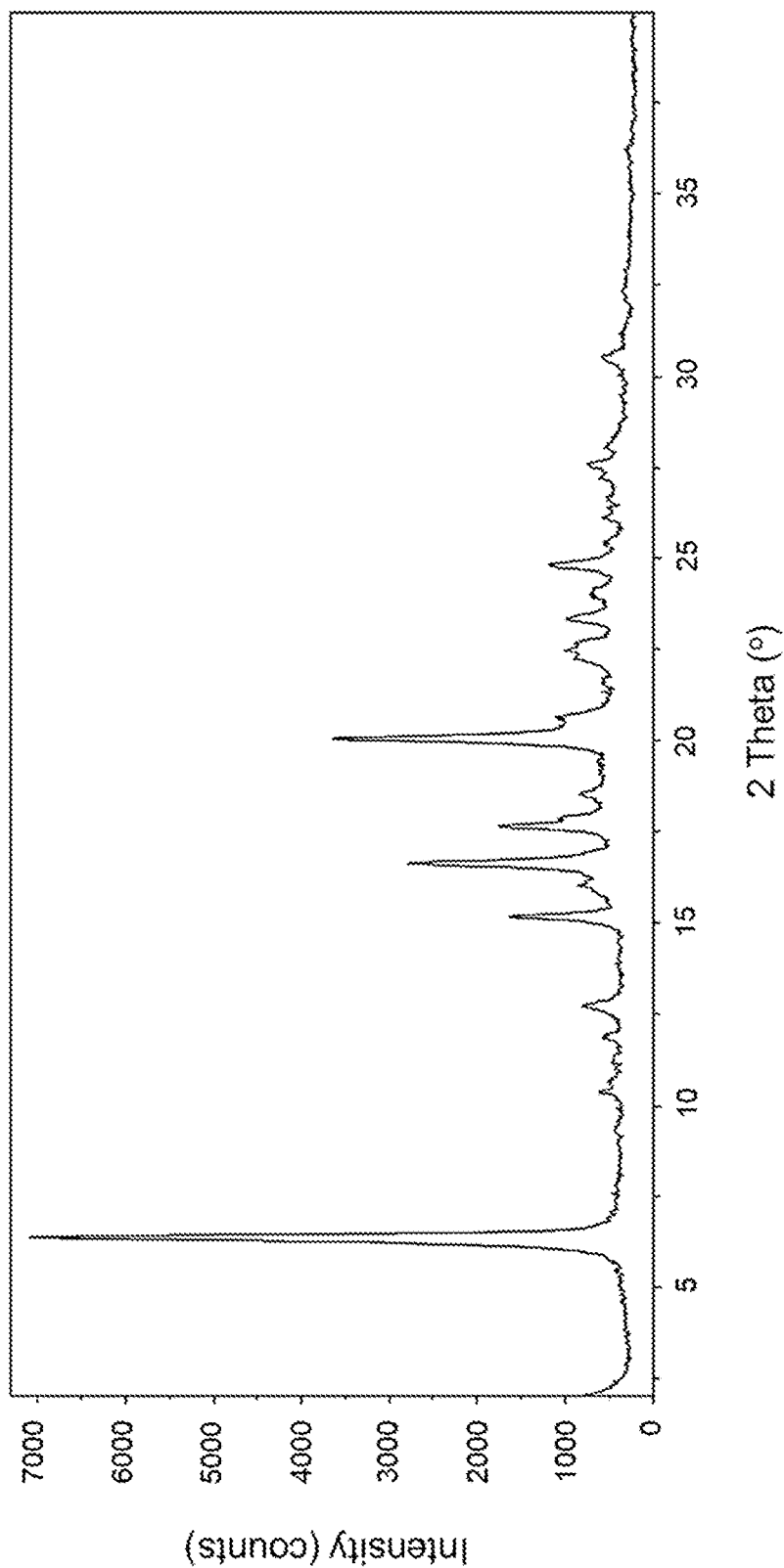
FIG. 3 shows an X-ray powder diffractogram for crystalline Form (II) of Compound (I), referred to as crystalline Form (II) herein, showing degrees 2θ (2-theta) on the X-axis and relative intensity on the Y-axis.

FIG. 3 shows an X-ray powder diffractogram for crystalline Form (II) of Compound (I).

Figure 4:
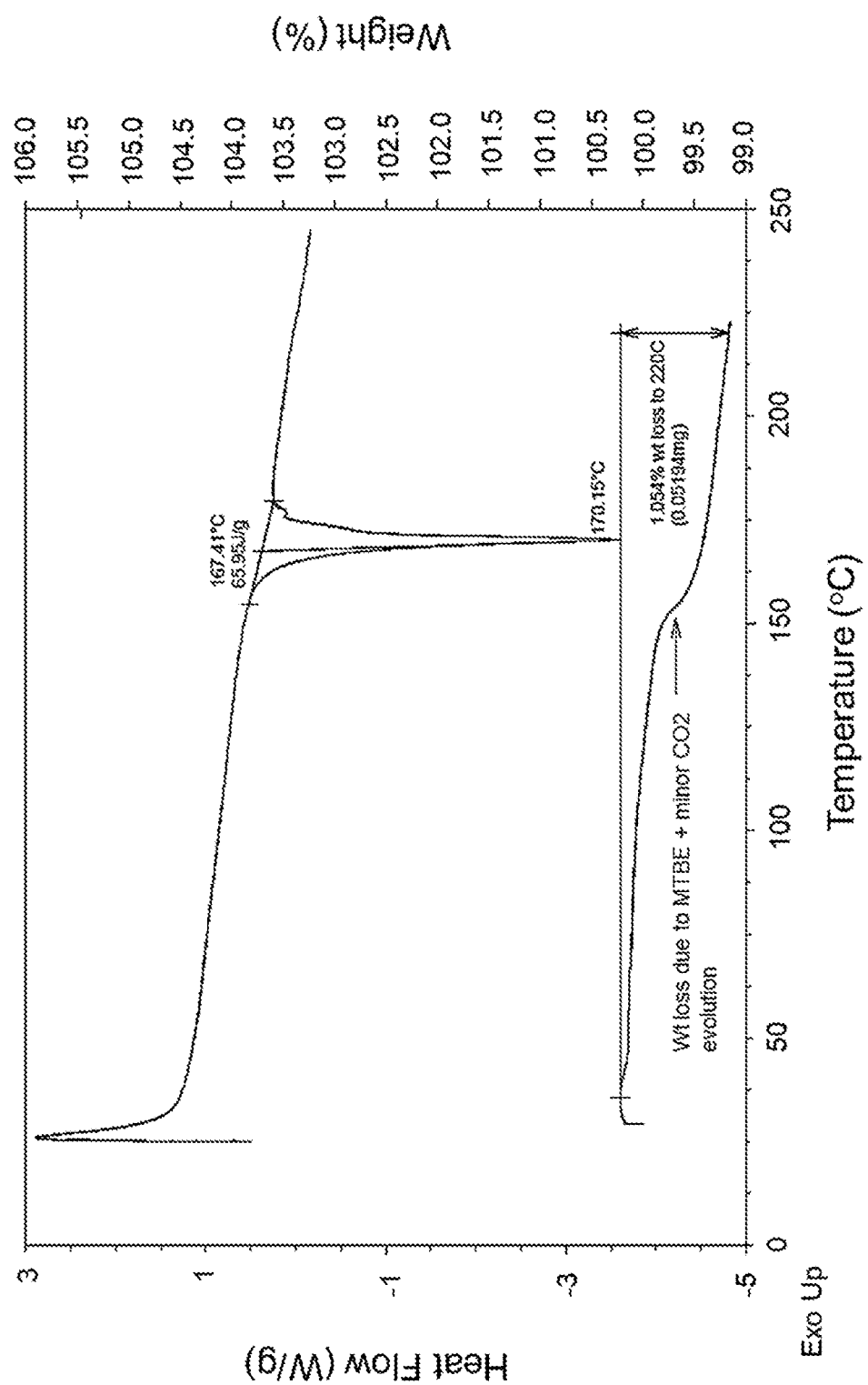
FIG. 4 shows a differential scanning calorimetry (DSC) thermogram and a thermogravimetric analysis (TGA) thermal curve for crystalline Form (II) of Compound (I).

FIG. 4 shows a DSC thermogram of crystalline Form (II) of Compound (I). In some embodiments, crystalline Form (II) of Compound (I) is characterized by a DSC thermogram having a peak endotherm (melting temperature) at about 170.0° C. to about 170.2° C. In some embodiments, crystalline Form (II) of Compound (I) is characterized by a DSC thermogram showing onset of melting/decomposition at about 167.2° C. to about 167.6° C. In some embodiments, the associated enthalpy is about 68 J/g (ΔH=68 J/g).

In some embodiments, crystalline Form (II) of Compound (I) is characterized by a DSC thermogram substantially similar to that in FIG. 4.

FIG. 4 also shows a TGA thermal curve for crystalline Form (II) of Compound (I). In some embodiments, crystalline Form (II) of Compound (I) is characterized by a mass loss of less than 1.5 wt. % between 35° C. and 220° C. by thermogravimetric analysis.

Crystalline Form (II) cannot be converted to crystalline Form (I) by heating and cooling.

In some embodiments, crystalline Form (I) of Compound (I) is characterized by an X-ray powder diffractogram generated by an X-ray powder diffraction analysis with an incident beam of Cu Kα radiation with signals substantially similar to those recited in Table 2.

TABLE 2

| 2-theta (deg) |
| --- |
| 6.32 |
| 8.87 |
| 9.32 |
| 10.38 |
| 10.60 |
| 11.22 |
| 11.86 |
| 12.71 |
| 15.18 |
| 16.04 |
| 16.63 |
| 16.96 |
| 17.67 |
| 17.91 |
| 18.54 |
| 19.18 |
| 20.05 |
| 20.64 |
| 21.64 |
| 22.27 |
| 22.51 |
| 22.72 |
| 23.33 |
| 24.03 |
| 24.83 |
| 25.42 |
| 26.12 |
| 26.34 |
| 26.68 |
| 27.24 |
| 27.55 |
| 28.05 |
| 28.36 |
| 29.37 |
| 30.03 |
| 30.53 |
| 32.11 |
| 32.33 |
| 34.12 |
| 36.20 |
| 39.24 |

In some embodiments, crystalline Form (II) of Compound (I) is characterized by an X-ray powder diffractogram having a signal at 6.3±0.2 degrees two-theta. In some embodiments, crystalline Form (II) of Compound (I) is characterized by an X-ray powder diffractogram having a signal at 15.2±0.2 degrees two-theta. In some embodiments, crystalline Form (II) of Compound (I) is characterized by an X-ray powder diffractogram having a signal at 16.0±0.2 degrees two-theta. In some embodiments, crystalline Form (II) of Compound (I) is characterized by an X-ray powder diffractogram having a signal at 16.6±0.2 degrees two-theta. In some embodiments, crystalline Form (II) of Compound (I) is characterized by an X-ray powder diffractogram having a signal at 17.7±0.2 degrees two-theta. In some embodiments, crystalline Form (II) of Compound (I) is characterized by an X-ray powder diffractogram having a signal at 20.0±0.2 degrees two-theta. In some embodiments, crystalline Form (II) of Compound (I) is characterized by an X-ray powder diffractogram having a signal at 24.8±0.2 degrees two-theta. In some embodiments, crystalline Form (II) of Compound (I) is characterized by an X-ray powder diffractogram having a signal at 27.5±0.2 degrees two-theta.

In some embodiments, crystalline Form (II) of Compound (I) is characterized by an X-ray powder diffractogram having a signal at two-theta values of 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least seven two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least six two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least five two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least four two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least three two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least two two-theta values chosen from 6.3±0.2, 15.2±0.2, 16.0±0.2, 16.6±0.2, 17.7±0.2, 20.0±0.2, 24.8±0.2, and 27.5±0.2. In some embodiments, crystalline Form (II) of Compound (I) is characterized by an X-ray powder diffractogram having a signal at at least one two-theta value chosen from 6.3±0.2, 15.2±0.2, 16.0±0.2, 16.6±0.2, 17.7±0.2, 20.0±0.2, 24.8±0.2, and 27.5±0.2.

In some embodiments, crystalline Form (II) of Compound (I) is characterized by an X-ray powder diffractogram substantially similar to that in FIG. 3.

In some embodiments, the present disclosure provides a process for preparing crystalline Form (II) of Compound (I). In some embodiments, the present disclosure provides crystalline Form (II) of Compound (I) prepared by a process comprising: dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether to form a solution. In some embodiments, the process further comprises stirring the solution to form a precipitate. In some embodiments, the process further comprises isolating crystalline Form (II) by filtration.

Crystalline Form (III) of Compound (I)

In some embodiments, the present disclosure provides crystalline Form (III) of Compound (I):

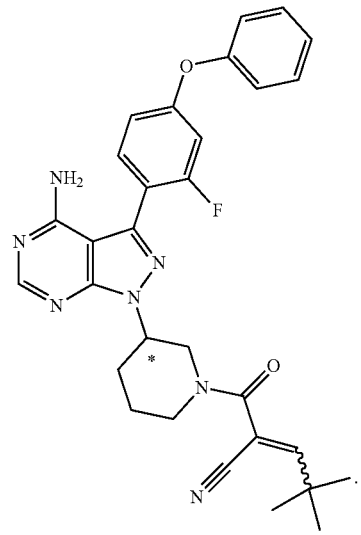

Figure 5:
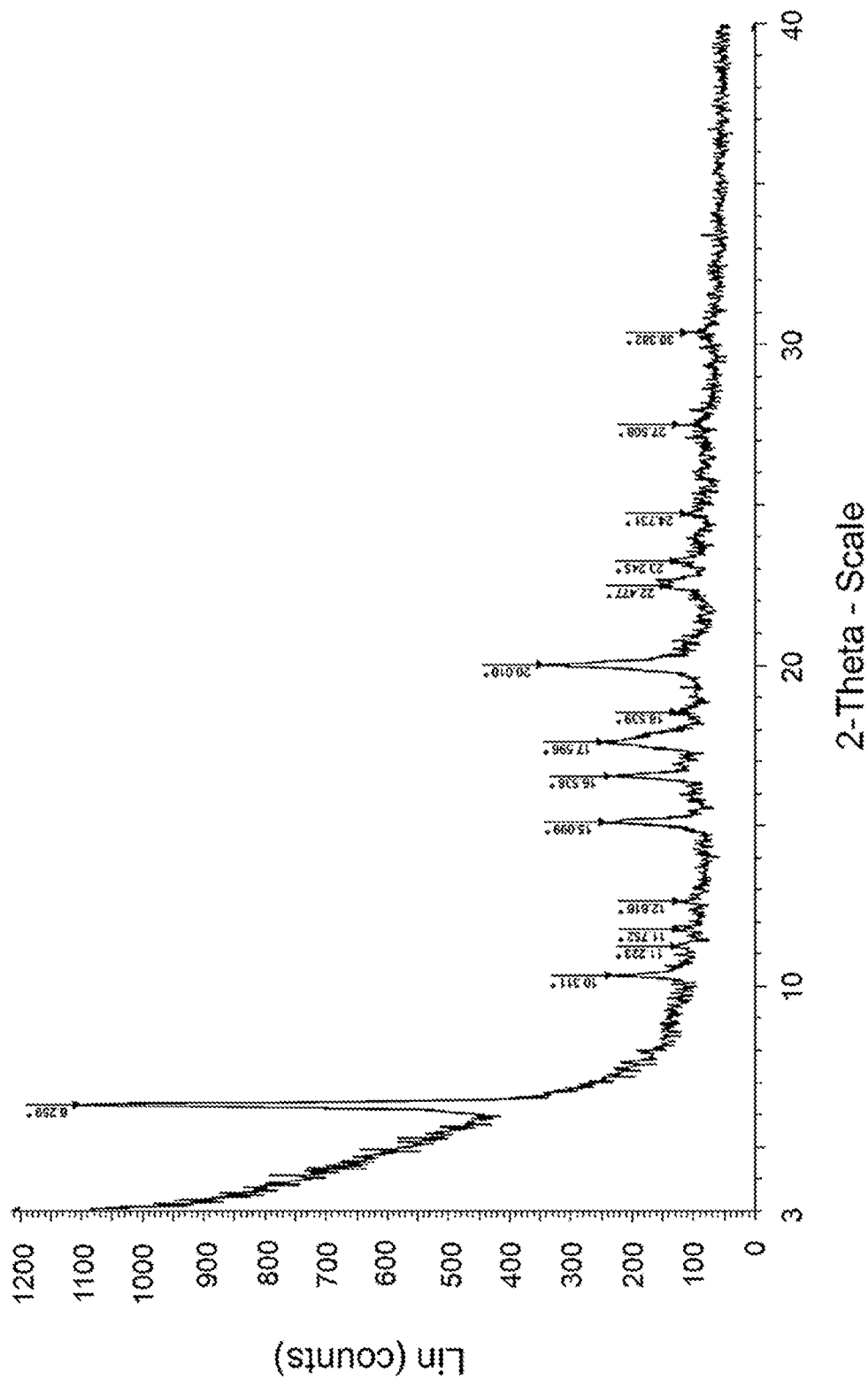
FIG. 5 shows an X-ray powder diffractogram for crystalline Form (III) of Compound (I), referred to as crystalline Form (III) herein, showing degrees 2θ (2-theta) on the X-axis and relative intensity on the Y-axis.

FIG. 5 shows an X-ray powder diffractogram for crystalline Form (III) of Compound (I).

Figure 6:
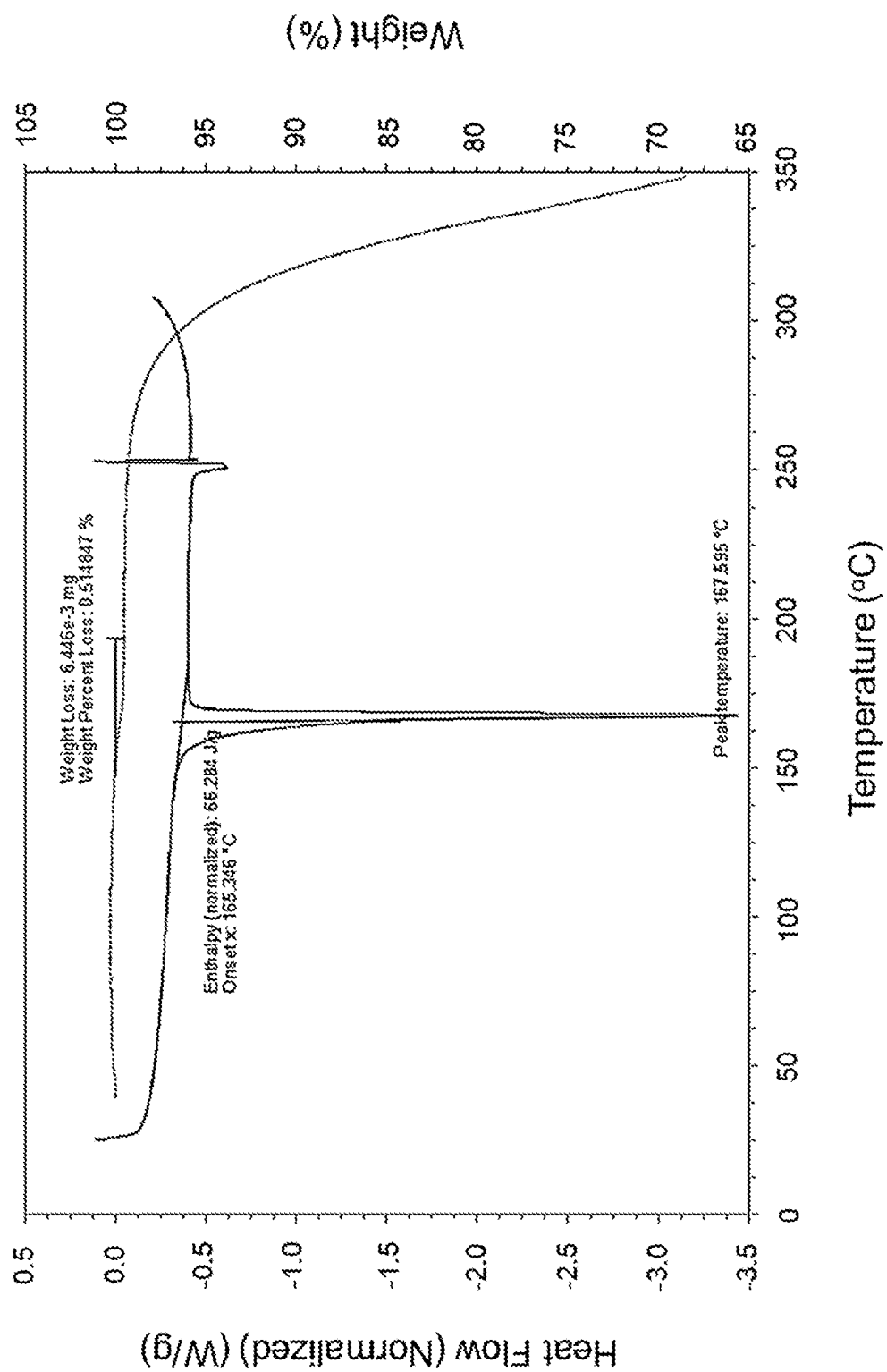
FIG. 6 shows a differential scanning calorimetry (DSC) thermogram and a thermogravimetric analysis (TGA) thermal curve for crystalline Form (III) of Compound (I).

FIG. 6 shows a DSC thermogram of crystalline Form (III) of Compound (I). In some embodiments, crystalline Form (III) of Compound (I) is characterized by a DSC thermogram having a peak endotherm (melting temperature) at about 167.4° C. to about 167.8° C. In some embodiments, crystalline Form (III) of Compound (I) is characterized by a DSC thermogram showing onset of melting/decomposition at about 165.1° C. to about 165.5° C. In some embodiments, crystalline Form (III) of Compound (I) is characterized by a DSC thermogram showing onset of melting at about 165.1° C. to about 165.5° C. In some embodiments, the associated enthalpy is about 66.3 J/g (ΔH=66.3 J/g).

In some embodiments, crystalline Form (III) of Compound (I) is characterized by a DSC thermogram substantially similar to that in FIG. 6.

FIG. 6 also shows a TGA thermal curve for crystalline Form (III) of Compound (I). In some embodiments, crystalline Form (III) of Compound (I) is characterized by mass loss of less than 0.6 wt. % between 50° C. and 190° C. by thermogravimetric analysis.

In some embodiments, crystalline Form (III) of Compound (I) is characterized by an X-ray powder diffractogram generated by an X-ray powder diffraction analysis with an incident beam of Cu Kα radiation with signals substantially similar to those recited in Table 3.

TABLE 3

| 2-theta (deg) |
| --- |
| 6.26 |
| 10.31 |
| 11.22 |
| 11.75 |
| 12.62 |
| 15.10 |
| 16.54 |
| 17.60 |
| 18.54 |
| 20.01 |
| 22.48 |
| 23.26 |
| 24.73 |

TABLE 3-continued

| 2-theta (deg) |
|---|
| 27.51 |
| 30.38 |

In some embodiments, crystalline Form (III) of Compound (I) is characterized by an X-ray powder diffractogram having a signal at 10.3±0.2 degrees two-theta. In some embodiments, crystalline Form (III) of Compound (I) is characterized by an X-ray powder diffractogram having a signal at 15.1±0.2 degrees two-theta. In some embodiments, crystalline Form (III) of Compound (I) is characterized by an X-ray powder diffractogram having a signal at 16.5±0.2 degrees two-theta. In some embodiments, crystalline Form (III) of Compound (I) is characterized by an X-ray powder diffractogram having a signal at 17.6±0.2 degrees two-theta. In some embodiments, crystalline Form (III) of Compound (I) is characterized by an X-ray powder diffractogram having a signal at 20.0±0.2 degrees two-theta. In some embodiments, crystalline Form (III) of Compound (I) is characterized by an X-ray powder diffractogram having a signal at 22.5±0.2 degrees two-theta.

In some embodiments, crystalline Form (III) of Compound (I) is characterized by an X-ray powder diffractogram having a signal at two-theta values of 10.3±0.2, 15.1±0.2, 16.5±0.2, 17.6±0.2, 20.0±0.2, and 22.5±0.2. In some embodiments, crystalline Form (III) of Compound (I) is characterized by an X-ray powder diffractogram having a signal at at least five two-theta values chosen from 10.3±0.2, 15.1±0.2, 16.5±0.2, 17.6±0.2, 20.0±0.2, and 22.5±0.2. In some embodiments, crystalline Form (III) of Compound (I) is characterized by an X-ray powder diffractogram having a signal at at least four two-theta values chosen from 10.3±0.2, 15.1±0.2, 16.5±0.2, 17.6±0.2, 20.0±0.2, and 22.5±0.2. In some embodiments, crystalline Form (III) of Compound (I) is characterized by an X-ray powder diffractogram having a signal at at least three two-theta values chosen from 10.3±0.2, 15.1±0.2, 16.5±0.2, 17.6±0.2, 20.0±0.2, and 22.5±0.2. In some embodiments, crystalline Form (III) of Compound (I) is characterized by an X-ray powder diffractogram having a signal at at least two two-theta values chosen from 10.3±0.2, 15.1±0.2, 16.5±0.2, 17.6±0.2, 20.0±0.2, and 22.5±0.2. In some embodiments, crystalline Form (III) of Compound (I) is characterized by an X-ray powder diffractogram having a signal at at least one two-theta value chosen from 10.3±0.2, 15.1±0.2, 16.5±0.2, 17.6±0.2, 20.0±0.2, and 22.5±0.2.

In some embodiments, crystalline Form (III) of Compound (I) is characterized by an X-ray powder diffractogram substantially similar to that in FIG. 5.

In some embodiments, the present disclosure provides a process for preparing crystalline Form (III) of Compound (I). In some embodiments, the present disclosure provides crystalline Form (III) of Compound (I) prepared by a process comprising: dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in methyl t-butyl ether. In some embodiments, the process further comprises isolating crystalline Form (III) by filtration.

Crystalline Form (IV) of Compound (I)

In some embodiments, the present disclosure provides crystalline Form (IV) of Compound (I):

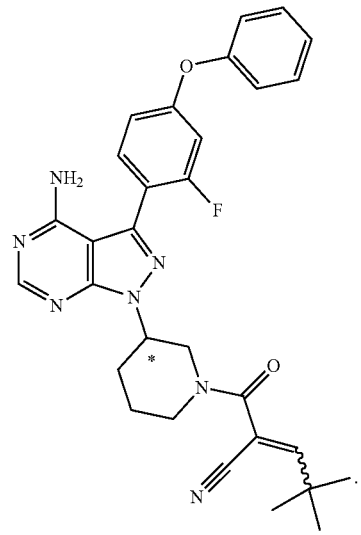 [SMILES: CC(C)(C)C=C(C#N)C(=O)N1CCCC(n2nc(-c3ccc(Oc4ccccc4)cc3F)c3c(N)ncnc32)C1]

(I)

Figure 7:
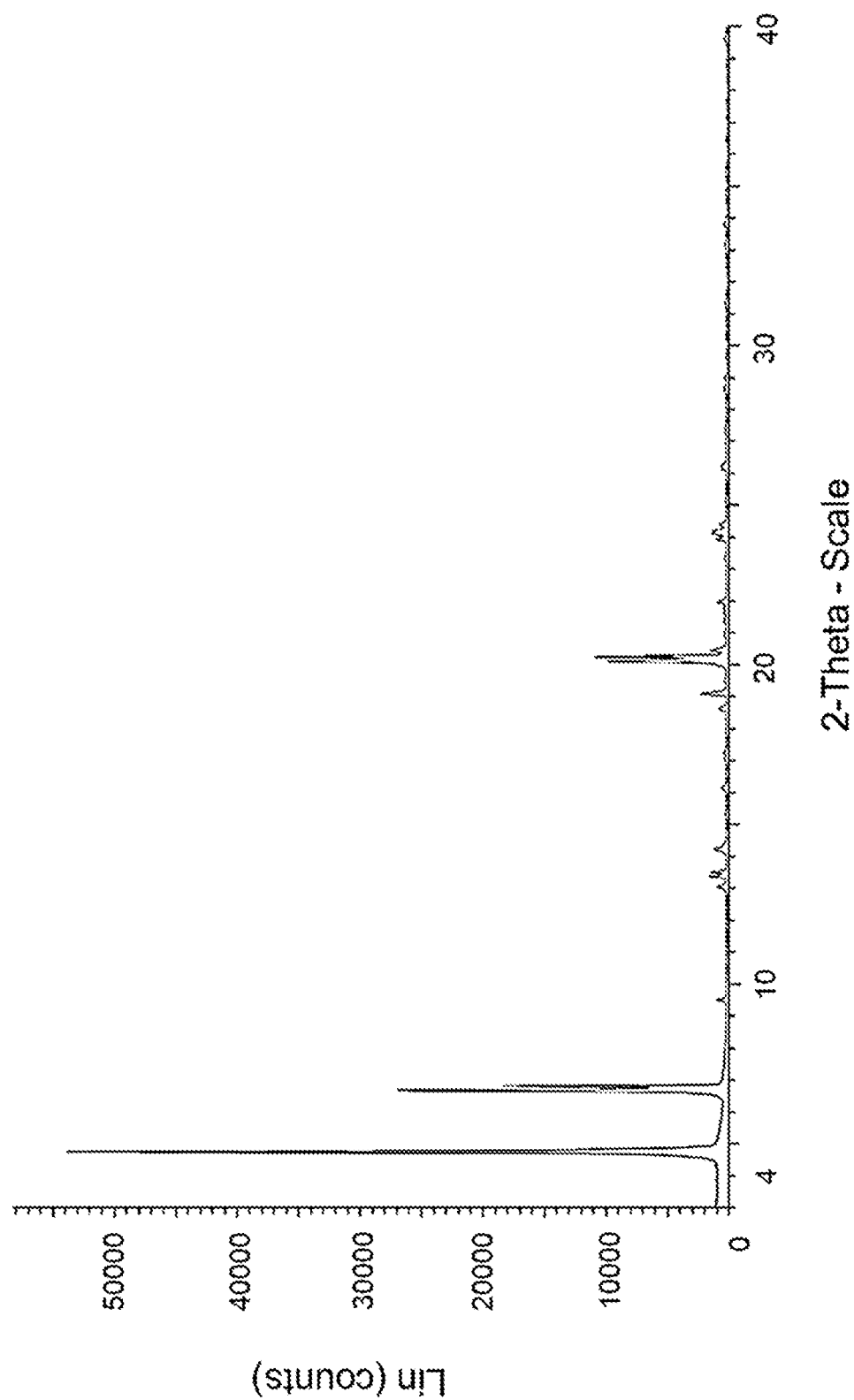
FIG. 7 shows an X-ray powder diffractogram for crystalline Form (IV) of Compound (I), referred to as crystalline Form (IV) herein, showing degrees 2θ (2-theta) on the X-axis and relative intensity on the Y-axis.

FIG. 7 shows an X-ray powder diffractogram for crystalline Form (IV) of Compound (I).

Figure 8:
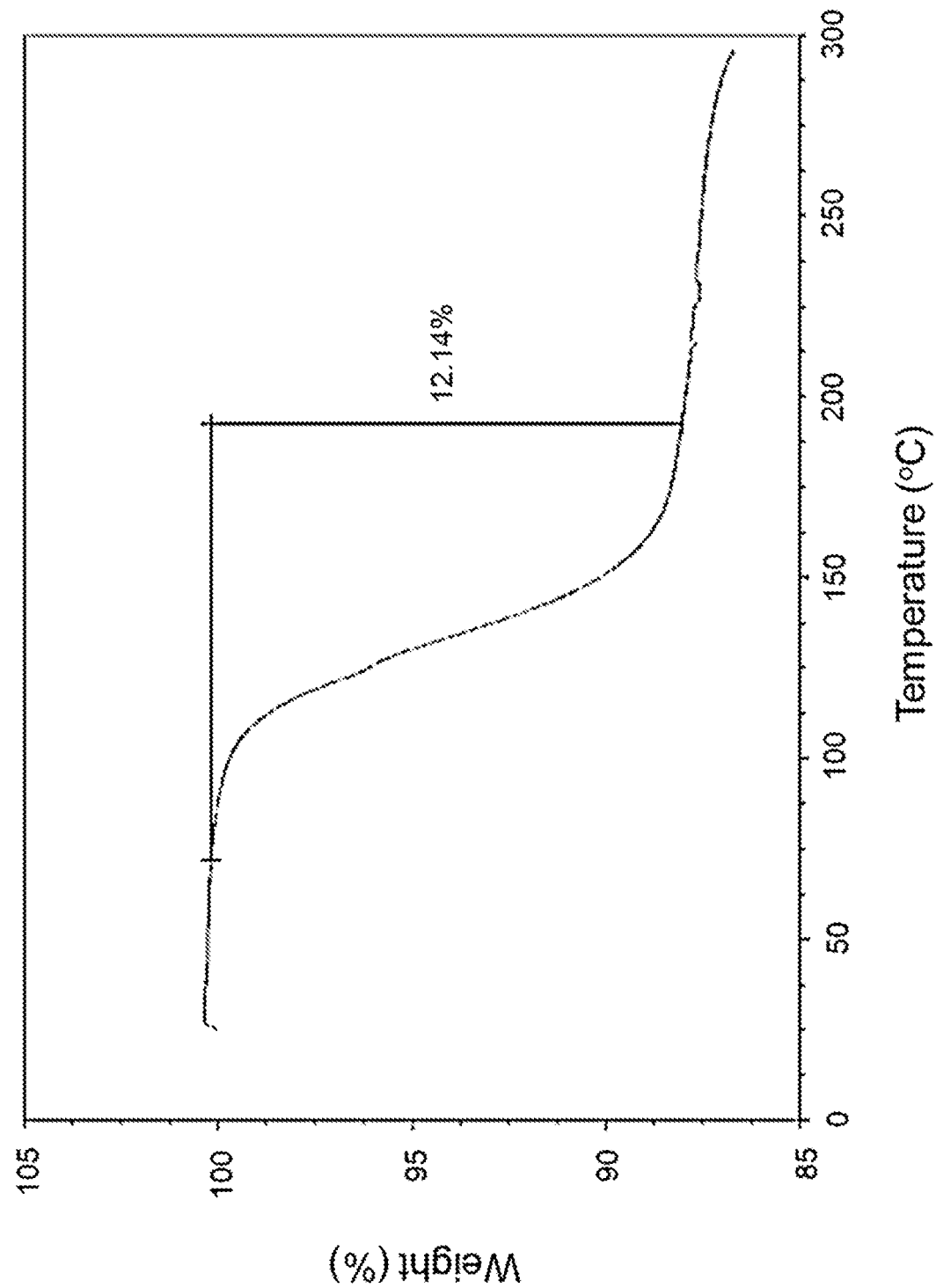
FIG. 8 shows a thermogravimetric analysis (TGA) thermal curve for crystalline Form (IV) of Compound (I).

FIG. 8 shows a TGA thermal curve for crystalline Form (IV) of Compound (I). In some embodiments, crystalline Form (IV) of Compound (I) is characterized by a mass loss of less than 14 wt. % between 70° C. and 180° C. by thermogravimetric analysis.

In some embodiments, crystalline Form (IV) of Compound (I) is characterized by an X-ray powder diffractogram generated by an X-ray powder diffraction analysis with an incident beam of Cu Kα radiation with signals substantially similar to those recited in Table 4.

TABLE 4

| 2-theta (deg) |
|---|
| 4.72 |
| 6.64 |
| 6.78 |
| 9.50 |
| 13.03 |
| 13.36 |
| 13.48 |
| 14.20 |
| 14.68 |
| 15.30 |
| 16.13 |
| 16.58 |
| 17.03 |
| 17.26 |
| 17.92 |
| 18.30 |
| 18.63 |
| 19.11 |
| 19.51 |
| 20.13 |
| 20.25 |
| 20.30 |
| 20.46 |
| 20.97 |
| 21.39 |
| 21.65 |
| 21.82 |
| 21.98 |
| 23.35 |
| 23.95 |
| 24.16 |
| 24.40 |
| 25.15 |

TABLE 4-continued

| 2-theta (deg) |
|---|
| 26.18 |
| 26.96 |
| 27.46 |
| 27.78 |
| 28.16 |
| 28.65 |
| 29.01 |
| 29.63 |
| 30.73 |
| 31.35 |
| 33.18 |
| 33.80 |
| 34.81 |
| 35.44 |
| 36.51 |
| 39.64 |

In some embodiments, crystalline Form (IV) of Compound (I) is characterized by an X-ray powder diffractogram having a signal at 4.7±0.2 degrees two-theta. In some embodiments, crystalline Form (IV) of Compound (I) is characterized by an X-ray powder diffractogram having a signal at 6.6±0.2 degrees two-theta. In some embodiments, crystalline Form (IV) of Compound (I) is characterized by an X-ray powder diffractogram having a signal at 6.8±0.2 degrees two-theta. In some embodiments, crystalline Form (IV) of Compound (I) is characterized by an X-ray powder diffractogram having a signal at 13.4±0.2 degrees two-theta. In some embodiments, crystalline Form (IV) of Compound (I) is characterized by an X-ray powder diffractogram having a signal at 13.5±0.2 degrees two-theta. In some embodiments, crystalline Form (IV) of Compound (I) is characterized by an X-ray powder diffractogram having a signal at 20.1±0.2 degrees two-theta. In some embodiments, crystalline Form (IV) of Compound (I) is characterized by an X-ray powder diffractogram having a signal at 20.2±0.2 degrees two-theta. In some embodiments, crystalline Form (IV) of Compound (I) is characterized by an X-ray powder diffractogram having a signal at 20.3±0.2 degrees two-theta. In some embodiments, crystalline Form (IV) of Compound (I) is characterized by an X-ray powder diffractogram having a signal at 24.2±0.2 degrees two-theta.

In some embodiments, crystalline Form (IV) of Compound (I) is characterized by an X-ray powder diffractogram having a signal at two-theta values of 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least eight two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least seven two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least six two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least five two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least four two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least three two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least two two-theta values chosen from 4.7±0.2, 6.6±0.2, 6.8±0.2, 13.4±0.2, 13.5±0.2, 20.1±0.2, 20.2±0.2, 20.3±0.2, and 24.2±0.2. In some embodiments, crystalline Form (IV) of Compound (I) is characterized by an X-ray powder diffractogram having a signal at at least one two-theta value chosen from 4.7±0.2, 6.6±0.2, 6.8±0.2, 13.4±0.2, 13.5±0.2, 20.1±0.2, 20.2±0.2, 20.3±0.2, and 24.2±0.2.

In some embodiments, crystalline Form (IV) of Compound (I) is characterized by an X-ray powder diffractogram substantially similar to that in FIG. 7.

In some embodiments, the present disclosure provides a process for preparing crystalline Form (IV) of Compound (I). In some embodiments, the present disclosure provides crystalline Form (IV) of Compound (I) prepared by a process comprising: dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in 2-methyl-1-propanol to form a solution. In some embodiments, the process further comprises filtering the solution. In some embodiments, the process further comprises isolating crystalline Form (IV) by evaporating the 2-methyl-1-propanol.

Crystalline Form (V) of Compound (I)

In some embodiments, the present disclosure provides crystalline Form (V) of Compound (I):

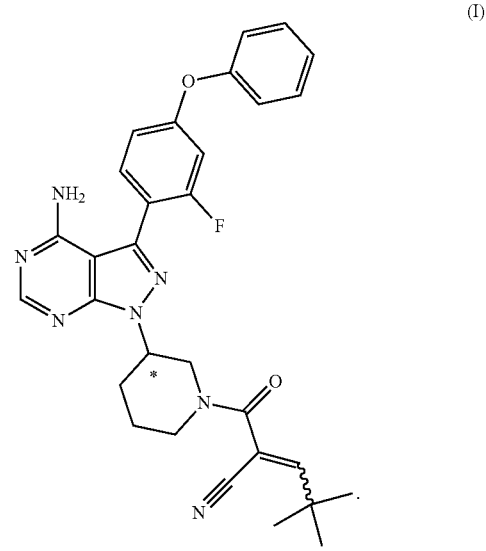 [SMILES: CC(C)(C)C=C(C#N)C(=O)N1CCCC(n2nc(-c3ccc(Oc4ccccc4)cc3F)c3c(N)ncnc32)C1]

(I)

Figure 9:
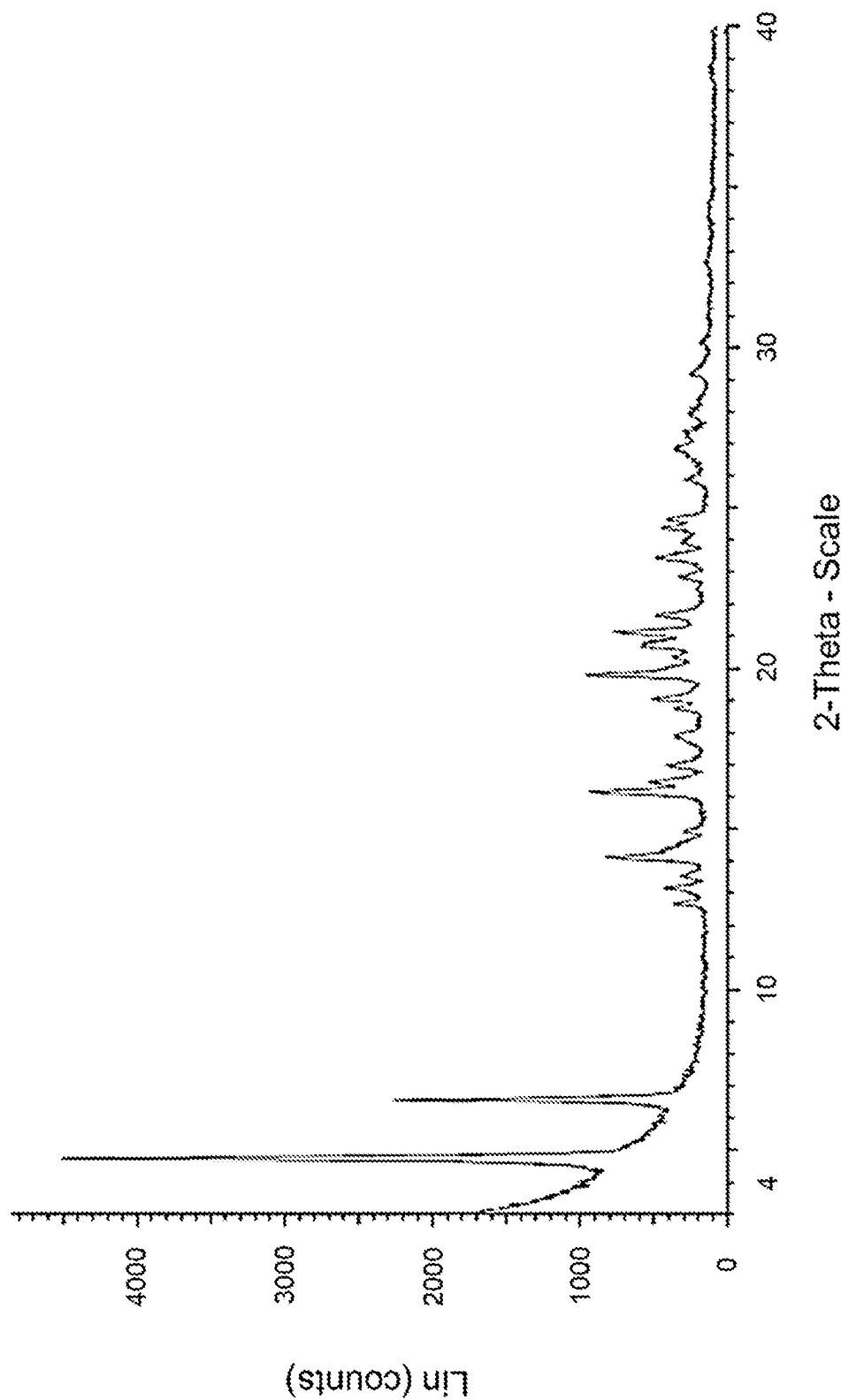
FIG. 9 shows an X-ray powder diffractogram for crystalline Form (V) of Compound (I), referred to as crystalline Form (V) herein, showing degrees 2θ (2-theta) on the X-axis and relative intensity on the Y-axis.

FIG. 9 shows an X-ray powder diffractogram for crystalline Form (V) of Compound (I).

Figure 10:
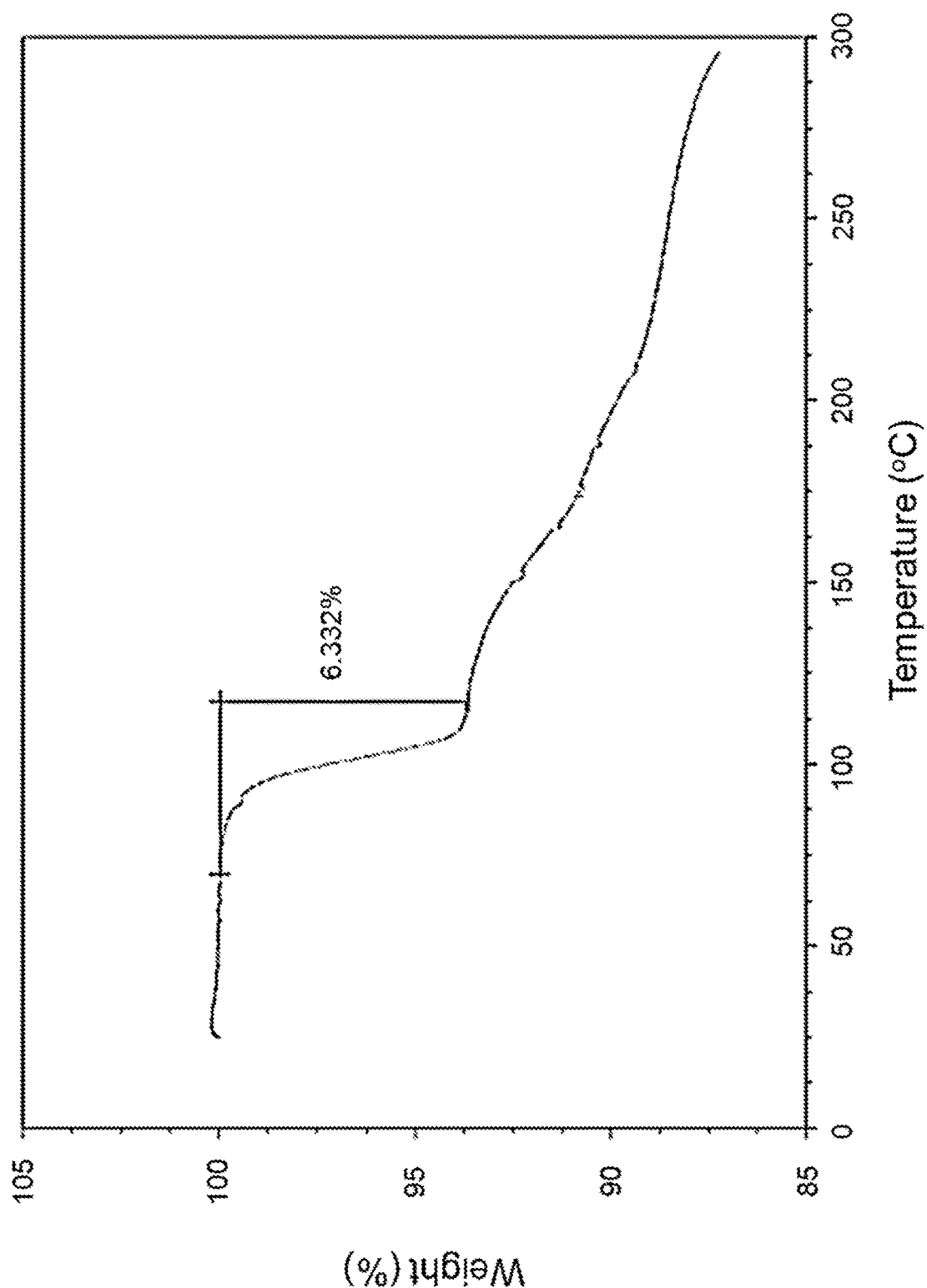
FIG. 10 shows a thermogravimetric analysis (TGA) thermal curve for crystalline Form (V) of Compound (I).

FIG. 10 shows a TGA thermal curve for crystalline Form (V) of Compound (I). In some embodiments, crystalline Form (V) of Compound (I) is characterized by a mass loss of less than 7 wt. % between 75° C. and 110° C. by thermogravimetric analysis.

In some embodiments, crystalline Form (V) of Compound (I) is a white solid.

In some embodiments, crystalline Form (V) of Compound (I) is characterized by an X-ray powder diffractogram generated by an X-ray powder diffraction analysis with an incident beam of Cu Kα radiation with signals substantially similar to those recited in Table 5.

TABLE 5

| 2-theta (deg) |
| --- |
| 4.72 |
| 6.54 |
| 12.67 |
| 13.15 |
| 13.53 |
| 14.11 |
| 14.94 |
| 16.15 |
| 16.47 |
| 16.97 |
| 17.90 |
| 18.76 |
| 19.07 |
| 19.82 |
| 20.36 |
| 20.74 |
| 21.13 |
| 21.67 |
| 22.85 |
| 23.46 |
| 23.94 |
| 24.40 |
| 24.67 |
| 25.9 |
| 26.86 |
| 27.31 |
| 27.95 |
| 29.21 |
| 30.18 |

In some embodiments, crystalline Form (V) of Compound (I) is characterized by an X-ray powder diffractogram having a signal at 4.7±0.2 degrees two-theta. In some embodiments, crystalline Form (V) of Compound (I) is characterized by an X-ray powder diffractogram having a signal at 6.5±0.2 degrees two-theta. In some embodiments, crystalline Form (V) of Compound (I) is characterized by an X-ray powder diffractogram having a signal at 14.2±0.2 degrees two-theta. In some embodiments, crystalline Form (V) of Compound (I) is characterized by an X-ray powder diffractogram having a signal at 16.2±0.2 degrees two-theta. In some embodiments, crystalline Form (V) of Compound (I) is characterized by an X-ray powder diffractogram having a signal at 16.5±0.2 degrees two-theta. In some embodiments, crystalline Form (V) of Compound (I) is characterized by an X-ray powder diffractogram having a signal at 19.8±0.2 degrees two-theta. In some embodiments, crystalline Form (V) of Compound (I) is characterized by an X-ray powder diffractogram having a signal at 20.7±0.2 degrees two-theta.

In some embodiments, crystalline Form (V) of Compound (I) is characterized by an X-ray powder diffractogram having a signal at two-theta values of 4.7±0.2, 6.5±0.2, 14.2±0.2, 16.2±0.2, 16.5±0.2, 19.8±0.2, and 20.7±0.2. In some embodiments, crystalline Form (V) of Compound (I) is characterized by an X-ray powder diffractogram having a signal at at least six two-theta values chosen from 4.7±0.2, 6.5±0.2, 14.2±0.2, 16.2±0.2, 16.5±0.2, 19.8±0.2, and 20.7±0.2. In some embodiments, crystalline Form (V) of Compound (I) is characterized by an X-ray powder diffractogram having a signal at at least five two-theta values chosen from 4.7±0.2, 6.5±0.2, 14.2±0.2, 16.2±0.2, 16.5±0.2, 19.8±0.2, and 20.7±0.2. In some embodiments, crystalline Form (V) of Compound (I) is characterized by an X-ray powder diffractogram having a signal at at least four two-theta values chosen from 4.7±0.2, 6.5±0.2, 14.2±0.2, 16.2±0.2, 16.5±0.2, 19.8±0.2, and 20.7±0.2. In some embodiments, crystalline Form (V) of Compound (I) is characterized by an X-ray powder diffractogram having a signal at at least three two-theta values chosen from 4.7±0.2, 6.5±0.2, 14.2±0.2, 16.2±0.2, 16.5±0.2, 19.8±0.2, and 20.7±0.2. In some embodiments, crystalline Form (V) of Compound (I) is characterized by an X-ray powder diffractogram having a signal at at least two two-theta values chosen from 4.7±0.2, 6.5±0.2, 14.2±0.2, 16.2±0.2, 16.5±0.2, 19.8±0.2, and 20.7±0.2. In some embodiments, crystalline Form (V) of Compound (I) is characterized by an X-ray powder diffractogram having a signal at at least one two-theta value chosen from 4.7±0.2, 6.5±0.2, 14.2±0.2, 16.2±0.2, 16.5±0.2, 19.8±0.2, and 20.7±0.2.

In some embodiments, crystalline Form (V) of Compound (I) is characterized by an X-ray powder diffractogram substantially similar to that in FIG. 9.

In some embodiments, the present disclosure provides a process for preparing crystalline Form (V) of Compound (I). In some embodiments, the present disclosure provides crystalline Form (V) of Compound (I) prepared by a process comprising: dissolving amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile in toluene to form a solution. In some embodiments, the method further comprises filtering the solution. In some embodiments, the method further comprises isolating crystalline Form (V) by evaporating the toluene.

Indications

Crystalline forms of Compound (I) described herein can be useful for treating conditions mediated by BTK activity in mammals. In some embodiments, crystalline forms of Compound (I) described herein may be used to treat humans or non-humans.

Crystalline forms of Compound (I) described herein may be useful in treating various conditions or diseases, such as, e.g., pemphigus vulgaris, pemphigus *foliaceus*, immune thrombocytopenia, cutaneous lupus, cutaneous lupus erythematosus, dermatitis, alopecia areata, vitiligo, pyoderma gangrenosum, membrane pemphigoid, epidermolysis bullosa acquisita, Steven Johnson syndrome, TEN Toxic epidermal necrolysis, drug eruptions, folliculitis decalvans, pseudofolliculitis barbae, leucoclastic vasculitis, hidradenitis suppurativa, palmar platar pustulosis, Lichenoid dermatitis, acne, mycosis fungoides, sweet syndrome, inflammatory bowel disease, arthritis, lupus, lupus nephritis, rheumatoid arthritis, psoriatic arthritis, juvenile arthritis, Sjogren's syndrome, multiple sclerosis, ankylosing spondylitisis, scleroderma, Wegener's granulomatosis, psoriasis, asthma, colitis, conjunctivitis, dermatitis, uveitis, eczema, diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, non-Hodgkin lymphoma, intravascular large B cell lymphoma, primary effusion lymphoma, burkitt lymphoma/leukemia, and lymphomatoid granulomatosis.

Pemphigus is a rare B cell-mediated autoimmune disease that causes debilitating intraepithelial blisters and erosions on the skin and/or mucous membranes. Pemphigus carries a 10% mortality, generally due to infections arising from compromised tissues and treatment side effects and affects approximately 0.1 to 0.5 people out of 100,000 each year (Scully et al., 2002; Scully et al., 1999). The characteristic intraepidermal blisters observed in pemphigus patients are caused by the binding of IgG autoantibodies to certain keratinocyte desmosomal adhesion proteins, desmogleins 1 and 3 (Dsg1 and Dsg3), resulting in loss of cell adhesion (Amagai M et al., 2012; Diaz L A et al., 2000). B cells play key roles in the production of these autoantibodies and in cellular tolerance mechanisms.

Immune thrombocytopenia (commonly referred to as ITP) is characterized by autoantibody-mediated destruction of platelets and impaired platelet production, which result in thrombocytopenia and a predisposition to bleeding associated with morbidity and mortality. There is preliminary evidence to support the role of BTK inhibition in patients with autoimmune cytopenias (Rogers 2016, Montillo 2017), where sequential episodes of severe autoimmune hemolytic anemia and ITP ceased after initiation of treatment with ibrutinib, a BTK/EGFR/ITK inhibitor, in patients with chronic lymphatic leukemia (CLL).

Pharmaceutical Compositions

The crystalline forms described herein are useful as active pharmaceutical ingredients (APIs), as well as materials for preparing pharmaceutical compositions that incorporate one or more pharmaceutically acceptable excipients and are suitable for administration to human subjects. In some embodiments, these pharmaceutical compositions will be a pharmaceutical product, such as, e.g., a solid oral dosage form, such as tablets and/or capsules.

In some embodiments, the present disclosure provides a pharmaceutical composition comprising at least one crystalline form of Compound (I). In some embodiments, the present disclosure provides a pharmaceutical composition comprising at least one crystalline form of Compound (I) and at least one additional pharmaceutically acceptable excipient. Each excipient must be "pharmaceutically acceptable" in the sense of being compatible with the subject composition and its components not injurious to the patient. Except insofar as any conventional pharmaceutically acceptable excipient is incompatible with Compound (I), such as by producing any undesirable biological effect or otherwise interacting in a deleterious manner with any other component(s) of the pharmaceutically acceptable composition, its use is contemplated to be within the scope of this disclosure.

Some non-limiting examples of materials which may serve as pharmaceutically acceptable excipients include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, also discloses additional non-limiting examples of pharmaceutically acceptable excipients, as well as known techniques for preparing and using the same.

Pharmaceutical compositions disclosed herein may be administered orally, parenterally, by inhalation spray, topically, rectally, nasally, buccally, vaginally, or via an implanted reservoir. The term "parenteral," as used herein includes subcutaneous, intravenous, intramuscular, intraarticular, intra-synovial, intrasternal, intrathecal, intrahepatic, intralesional, and intracranial injection or infusion techniques. In some embodiments, the compositions of the disclosure are administered orally, intraperitoneally, or intravenously. Sterile injectable forms of the pharmaceutical compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans, and other emulsifying agents or bioavailability enhancers which are commonly used in the manufacture of pharmaceutically acceptable solid, liquid, or other dosage forms may also be used for the purposes of formulation.

Pharmaceutical compositions disclosed herein may also be orally administered in any orally acceptable dosage form including, but not limited to, capsules, tablets, aqueous suspensions, or solutions. When aqueous suspensions are required for oral use, the active ingredient is typically combined with emulsifying and suspending agents. If desired, certain sweetening, flavoring, or coloring agents may also be added.

Alternatively, pharmaceutical compositions disclosed herein may be administered in the form of suppositories for rectal administration. Suppositories can be prepared by mixing the agent with a suitable non-irritating excipient that is solid at room temperature but liquid at rectal temperature and therefore will melt in the rectum to release the drug. Such materials include, but are not limited to, cocoa butter, beeswax, and polyethylene glycols.

The pharmaceutical compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation or in a suitable enema formulation. Topically-transdermal patches may also be used.

For topical applications, the pharmaceutical compositions may be formulated in a suitable ointment containing the active component suspended or dissolved in at least one excipient. Excipients for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, pharmaceutical compositions disclosed herein can be formulated in a suitable lotion or cream containing the active components suspended or dissolved in at least one pharmaceutically acceptable excipient. Suitable excipients include, but are not limited to, mineral oil, sorbitan monostearate, polysorbate 60, cetyl esters wax, cetearyl alcohol, 2-octyldodecanol, benzyl alcohol, and water.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosing

In general, crystalline forms of Compound (I) will be administered in a therapeutically effective amount by any of the accepted modes of administration for agents that serve similar utilities. The effective dose for any particular mammal (e.g., any particular human) will depend upon a variety of factors including: the disorder being treated and the severity of the disorder; the specific pharmaceutical composition employed; the age, body weight, general health, sex and diet of the mammal; the time of administration, route of administration, the duration of the treatment; and like factors well known in the medical arts. In some embodiments, a therapeutically effective amount of at least one crystalline form of Compound (I) is administered to a mammal in need thereof. Therapeutically effective amounts of the crystalline forms disclosed herein may range from 0.01 to 500 mg per kg patient body weight per day, which can be administered in single or multiple doses. A suitable dosage level may be 0.01 to 250 mg/kg per day, 0.05 to 100 mg/kg per day, or 0.1 to 50 mg/kg per day. Within this range, in some embodiments, the dosage can be 0.05 to 0.5, 0.5 to 5, or 5 to 50 mg/kg per day. For oral administration, in some embodiments, the compositions can be provided in the form of tablets containing 1.0 to 1000 milligrams of the active ingredient, e.g., 1, 5, 10, 15, 20, 25, 50, 75, 100, 150, 200, 250, 300, 400, 500, 600, 750, 800, 900, or 1000 milligrams of the active ingredient.

In general, crystalline forms of this disclosure will be administered as pharmaceutical compositions by any one of the following routes: oral; systemic (e.g., transdermal, intranasal, or by suppository); topical; or parenteral (e.g., intramuscular, intravenous, or subcutaneous) administration. Illustratively, compositions can take the form of tablets, capsules, semisolids, powders, sustained release formulations, enteric coated or delayed release formulations, solutions, suspensions, elixirs, aerosols, or any other appropriate compositions.

All publications and patents mentioned herein are hereby incorporated by reference in their entirety as if each individual publication or patent was specifically and individually indicated to be incorporated by reference.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those of ordinary skill in the art will recognize or be able to ascertain, using no more than routine experimentation, many equivalents to the specific embodiments of the disclosure described herein. Such equivalents are intended to be encompassed by the following claims.

EXAMPLES

The following examples are intended to be illustrative and are not meant in any way to limit the scope of the disclosure.

Analytical Method 1: Powder X-Ray Diffraction

Powder X-ray diffraction may be carried out with a Stoe Stadi P diffractometer equipped with a Mythen1K detector operating with Cu-Kα1 radiation. Measurements with this instrument may be performed in transmission at a tube voltage of 40 kV and 40 mA tube power. A curved Ge monochromator may be used for testing with Cu-Kα1 radiation. The following parameters may be set: 0.02° 2θ step size, 12 s step time, 1.5-50.5° 2θ scanning range, and 1°2θ detector step (detector mode in step scan). For a typical sample preparation, about 10 mg of sample is placed between two acetate foils and mounted into a Stoe transmission sample holder. The sample is rotated during the measurement. All sample preparation and measurement may be done in an ambient air atmosphere.

Analytical Method 2: Powder X-Ray Diffraction (PXRD) PANalytical

PXRD diffractograms may be acquired on PANalytical X'Pert Pro diffractometer using Ni-filtered Cu Kα (45 kV/40 mA) radiation and a step size of 0.03° 2q and X'celerator™ RTMS (Real Time Multi-Strip) detector. Configuration on the incidental beam side may be: variable divergence slits (10 mm irradiated length), 0.04 rad Soller slits, fixed anti-scatter slit (0.50°), and 10 mm beam mask. Configuration on the diffracted beam side may be: variable anti-scatter slit (10 mm observed length) and 0.04 rad Soller slit. Samples are mounted flat on zero-background Si wafers.

Analytical Method 3: Differential Scanning Calorimetry (DSC)

DSC may be conducted with a TA Instruments Q100 or Q2000 differential scanning calorimeter equipped with an autosampler and a refrigerated cooling system under 40 mL/min N2 purge. DSC thermograms of screening samples may be obtained at 15° C./min in crimped Al pans.

Analytical Method 4: Thermogravimetric Analysis (TGA)

TGA thermograms may be obtained with a TA Instruments Q50 thermogravimetric analyzer under 40 mL/min N2 purge in Pt or Al pans. TGA thermograms of screening samples may be obtained at 15° C./min.

Analytical Method 5: Thermogravimetric Analysis with IR Off-Gas Detection (TGA-IR)

TGA-IR may be conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA may be conducted with 25 mL/min N2 flow and heating rate of 15° C./min in Pt or Al pans. IR spectra may be collected at 4 cm$^{-1}$ resolution and 32 scans at each time point.

General Methods:

A crystal form screen of Compound (I) was performed using multiple solvents and three different crystallization techniques to yield multiple crystalline forms of Compound (I). In brief, the three different crystallization techniques were thermocycling (TC), rapidly cooling (RC), and slow evaporation (EV). To prepare crystalline forms of Compound (I) by thermocycling, slurries comprising Compound (I) were temperature-cycled between 5° C. and 40° C. for 36 hours, followed by equilibration at 25° C. for 8 hours. To prepare crystalline forms of Compound (I) through rapid cooling, clarified saturated solutions of Compound (I) were rapidly cooled from 25° C. to 4° C. and held at 4° C. for 48 hours. To prepare crystalline forms of Compound (I) by slow evaporation, solutions comprising Compound (I) were slowly evaporated for up to ten days. Solvents and solvent systems yielding crystalline Forms (I), (II), and (V) are shown below in Table 6.

TABLE 6

| Solvent (w/v) | TC | RC | EV |
| --- | --- | --- | --- |
| Water | I | | |
| Methanol | I | | |
| 2-Methoxyethanol:Isopropyl ether (20:80) | I | | II |
| 1-Propanol | I | | II |
| Nitromethane | I | | II |
| Acetonitrile | I | | |
| Dimethyl sulfoxide:t-Butyl methyl ether (20:80) | | | |
| Acetone | I | | II |
| 2-Butanone | | I | I and II |
| Dichloromethane | | | |
| Methyl acetate:Heptane (20:80) | | | |
| 4-Methyl-2-pentanone | | | |
| Chloroform | | | |
| Ethyl acetate | I | | I and II |
| Chlorobenzene:Cyclohexane (20:80) | | | |
| Tetrahydrofuran | | | |
| 1,4-Dioxane | | | |

TABLE 6-continued

| Solvent (w/v) | TC | RC | EV |
| --- | --- | --- | --- |
| Isopropyl ether | II | | |
| Toluene | | | II and V |
| Cyclohexane | II | | |
| Heptane | II | | |
| 1-Butanol | I and II | | II |
| 2-Propanol | | | |
| Trifluoroethanol:Isopropyl ether (20:80) | II | | |
| Butyl Acetate | I | | |
| t-Butyl methyl ether | II | | |
| Isopropyl acetate | I | | II |
| Ethanol | I | | II |
| 1-Methoxy-2-propanol:Isopropyl ether (20:80) | I and II | | II |
| Cyclohexanone | | | |
| N,N-Dimethylformamide:Water (20:80) | II | | |
| 2-Methoxyethyl ether:Heptane (20:80) | II | | |
| Cyclopentyl methyl ether | I | | II |
| Acetonitrile:Water (95:5) | I | | I and II |
| Acetone:Water (95:5) | I | | II |
| Tetrahydrofuran:Water (95:5) | | | |
| 2-propanol:Water (95:5) | I | | |
| Methanol:Water (90:10) | I | | II |
| Acetonitrile:Water (90:10) | I | | II |
| Acetone:Water (90:10) | I | | II |
| 2-Me-THF | | | II |
| 1,4-Dioxane:Water (90:10) | | | |
| 2-propanol:Water (90:10) | I | | |
| Acetone:Water (80:20) | I | | |
| Ethanol:Water (20:80) | I | | |
| Ethyl acetate:Cyclohexane (20:80) | II | | |
| Acetonitrile:Isopropyl ethyl ether (20:80) | I | | |
| 4-Methyl-2-pentanone:Heptane (20:80) | II | | |

Example 1: Preparation of Crystalline Form (I) of Compound (I)

Methyl isobutyl ketone (MIBK; 6 mL) was added to amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (1.0 g) and stirred to form a solution. After approximately five minutes of agitation, a precipitate began to form. Additional MIBK (10 mL) was charged, and the slurry was stirred. After approximately ten days, the solid was filtered and rinsed with MIBK (10 mL). The solid was dried under vacuum with heating to afford approximately 0.5 g of crystalline Form (I) of Compound (I) as a white solid.

Example 2: Preparation of Crystalline Form (II) of Compound (I)

Amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile (1.0 g) was dissolved in methyl t-butyl ether (MTBE, 4 mL). The solution was stirred at room temperature. After approximately five minutes, precipitates began to form. The slurry was charged with additional MTBE (approximately 10 mL). The solid was filtered and dried under vacuum to give approximately 0.7 g of crystalline Form (II) of Compound (I).

Example 3: Preparation of Crystalline Form (III) of Compound (I)

Amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile was dissolved in methyl t-butyl ether (MTBE). The solution was stirred at room temperature. The solid was filtered and dried under vacuum to give crystalline Form (III) of Compound (I).

Example 4: Preparation of Crystalline Form (IV) of Compound (I)

Amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile was dissolved in 2-methyl-1-propanol. The solution was filtered, and the solvent was slowly evaporated and then dried to give a white solid. The dried solid was analyzed. The dried solid was analyzed and found to be crystalline Form (IV) of (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile.

Example 5: Preparation of Crystalline Form (V) of Compound (I)

Amorphous (R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile was dissolved in toluene. The solution was filtered, and the solvent was slowly evaporated and then dried to give a white solid. The solid was analyzed and identified as crystalline Form (V) of Compound (I).

What is claimed is:

1. Crystalline Form (I) of Compound (I):

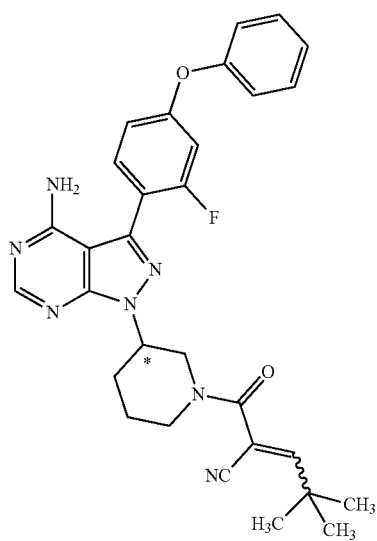

(I)

wherein crystalline Form (I) is characterized by an X-ray powder diffractogram comprising at least one signal at a value (°2θ) chosen from 6.3°±0.2 °2θ, 12.6°±0.2 °2θ, 16.2°±0.2 °2θ, 17.6°±0.2 °2θ, 18.2°±0.2 °2θ, 18.4°±0.2 °2θ, and 22.1°±0.2 °2θ.

2. The crystalline Form (I) according to claim 1, wherein the crystalline Form (I) is further characterized by an X-ray powder diffractogram comprising at least three signals at values (°2θ) chosen from 6.3°±0.2 °2θ, 12.6°±0.2 °2θ, 16.2°±0.2 °2θ, 17.6°±0.2 °2θ, 18.2°±0.2 °2θ, 18.4°±0.2 °2θ, and 22.1°±0.2 °2θ.

3. The crystalline Form (I) according to claim 1, wherein the crystalline Form (I) is further characterized by any one of the following:

(i) a differential scanning calorimetry thermogram showing onset of melting at about 174.8° C. to about 175.2° C.; or (ii) a differential scanning calorimetry thermogram having an endothermic peak at about 177° C. to about 178° C.; or (iii) a differential scanning calorimetry thermogram showing onset of melting at about 174.8° C. to about 175.2° C. and a differential scanning calorimetry thermogram having an endothermic peak at about 177° C. to about 178° C.

4. The crystalline Form (I) according to claim 1, wherein at least 95% by weight of the crystalline Form (I) of Compound (I) is the (R) enantiomer.

5. The crystalline Form (I) according to claim 1, wherein at least 95% by weight of the crystalline Form (I) of Compound (I) is the (E) diastereomer.

6. A pharmaceutical composition comprising at least one pharmaceutically acceptable excipient and the crystalline Form (I) according to claim 1.

* * * * *